United States Patent
Nguyen et al.

(10) Patent No.: US 11,276,479 B2
(45) Date of Patent: Mar. 15, 2022

(54) TUMOR ANTIGENICITY PROCESSING AND PRESENTATION

(71) Applicants: NANTOMICS, LLC, Culver City, CA (US); NANT HOLDINGS IP, LLC, Culver City, CA (US)

(72) Inventors: Andrew Nguyen, Culver City, CA (US); John Zachary Sanborn, Culver City, CA (US); Charles Joseph Vaske, Culver City, CA (US); Shahrooz Rabizadeh, Culver City, CA (US); Kayvan Niazi, Culver City, CA (US); Patrick Soon-Shiong, Culver City, CA (US); Stephen Charles Benz, Culver City, CA (US)

(73) Assignees: Nantomics, LLC, Culver City, CA (US); Nant Holdings IP, LLC, Culver City, CA (US)

(*) Notice: Subject to any disclaimer, the term of this patent is extended or adjusted under 35 U.S.C. 154(b) by 176 days.

(21) Appl. No.: 16/465,997

(22) PCT Filed: Nov. 30, 2017

(86) PCT No.: PCT/US2017/064078
§ 371 (c)(1),
(2) Date: May 31, 2019

(87) PCT Pub. No.: WO2018/102613
PCT Pub. Date: Jun. 7, 2018

(65) Prior Publication Data
US 2020/0082906 A1    Mar. 12, 2020

Related U.S. Application Data

(60) Provisional application No. 62/428,945, filed on Dec. 1, 2016.

(51) Int. Cl.
*G16B 20/50* (2019.01)
*G16B 30/00* (2019.01)

(52) U.S. Cl.
CPC ............. *G16B 20/50* (2019.02); *G16B 30/00* (2019.02)

(58) Field of Classification Search
CPC ................................ G16B 20/50; G16B 30/00
USPC ........................................................ 702/19
See application file for complete search history.

(56) References Cited

U.S. PATENT DOCUMENTS

| 7,473,532 B2 | 1/2009 | Darfler et al. |
| 2012/0059670 A1 | 3/2012 | Sanborn et al. |
| 2012/0066001 A1 | 3/2012 | Sanborn et al. |
| 2016/0331822 A1 | 11/2016 | Hacohen et al. |
| 2016/0339090 A1 | 11/2016 | Hacohen et al. |
| 2017/0212984 A1 | 7/2017 | Yelensky et al. |

FOREIGN PATENT DOCUMENTS

| CA | 3 045 811 A1 | 6/2018 |
| CN | 110214275 A | 9/2019 |
| JP | 2020-507557 A | 3/2020 |
| KR | 10-2015-0143597 A | 12/2015 |
| KR | 10-2019-0083671 A | 7/2019 |
| WO | 2014/012051 A1 | 1/2014 |
| WO | 2015/103037 A2 | 7/2015 |
| WO | 2016/174085 A1 | 11/2016 |
| WO | 2016/187508 A2 | 11/2016 |
| WO | 2016187508 A2 | 11/2016 |
| WO | 2017/035392 A1 | 3/2017 |
| WO | 2017100338 A1 | 6/2017 |
| WO | 2018/102613 A2 | 6/2018 |

OTHER PUBLICATIONS

Notice of Final Rejection received for Korean Patent Application Serial No. 1020197018904 dated Oct. 5, 2020, 2 pages (Including English Translation).
Extended European Search Report received for the European Application Serial No. EP17876742.2, dated Jul. 7, 2020, 9 pages.
Examination report No. 1 received for Australian Patent Application Serial No. 2017367696 dated Sep. 30, 2020, 4 pages.
Lawrence et al., "Discovery and saturation analysis of cancer genes across 21 tumour types", Nature, 2014, vol. 505, No. 7484, pp. 495-501.
Reimand et al., "Systematic analysis of somatic mutations in phosphorylation signaling predicts novel cancer drivers", Molecular Systems Biology, 2014, vol. 9, No. 637, 18 pages.
Dees et al., "MuSiC: Identifying mutational significance in cancer genomes", Genome Research, 2012, vol. 22, No. 8, pp. 1589-1598.
Tamborero et al., "OncodriveCLUST: exploiting the positional clustering of somatic mutations to identify cancer genes", Bioinformatics, 2013, vol. 29, No. 18, pp. 2238-2244.
Gonzalez-Perez et al., "Functional impact bias reveals cancer drivers", Nucleic Acids Research, 2012, vol. 40, No. 21, e169, 10 pages.
Mularoni et al., "OncodriveFML: a general framework to identify coding and non-coding regions with cancer driver mutations", Genome Biology, 2016, vol. 17, No. 128, 13 pages.

(Continued)

*Primary Examiner* — Jerry Lin
(74) *Attorney, Agent, or Firm* — Martin Fessenmaier; Umberg Zipser LLP

(57) ABSTRACT

Methods for targeting a tumor antigen for immunotherapy based on HLA allele type and the mutations present in the tumor antigen are presented. A patient's HLA allele type and a tumor antigen derived from a mutation in cancer driver gene can be matched with a majority allele type having a minimum affinity to the same tumor antigen or with those of a plurality of patients with a history of cancer treatment. Upon matching, a cancer treatment against the tumor antigen can be selected and administered to the patient to achieve a desired effect.

8 Claims, 3 Drawing Sheets
Specification includes a Sequence Listing.

(56) References Cited

OTHER PUBLICATIONS

Davoli et al., "Cumulative Haploinsufficiency and Triplosensitivity Drive Aneuploidy Patterns and Shape the Cancer Genome", Cell, 2013, vol. 155, No. 4, pp. 948-962.
Schroeder et al., "OncodriveROLE classifies cancer driver genes in loss of function and activating mode of action", Bioinformatics, 2014, vol. 30, No. 17, pp. i549-i555.
Vaske et al., "Inference of patient-specific pathway activities from multi-dimensional cancer genomics data using PARADIGM", Bioinformatics, 2010, vol. 26, No. 12, pp. i237-i245.
Ng et al., "PARADIGM-SHIFT predicts the function of mutations in multiple cancers using pathway impact analysis", Bioinformatics, 2012, vol. 28, No. 18, pp. i640-i646.
Rubio-Perez et al., "In Silico Prescription of Anticancer Drugs to Cohorts of 28 Tumor Types Reveals Targeting Opportunities", Cancer Cell, 2015, vol. 27, No. 3, pp. 382-396.
Zhang et al., "Machine learning competition in immunology—Prediction of HLA class I binding peptides", Journal of Immunological Methods, 2011, vol. 374, pp. 1-4.
Office Action received for Canadian Application Serial No. 3045811, dated Jun. 10, 2020, 6 pages.
Rajasagi et al., "Systematic identification of personal tumor-specific neoantigens in chronic lymphocytic leukemia", Blood, 2014, vol. 124, No. 3, pp. 453-462.
Van et al., "High sensitivity of cancer exome-based CD8 T cell neo-antigen identification", OncoImmunology, 2014, vol. 3, No. 5 (e28836), 6 pages.
Robbins et al., "Mining exomic sequencing data to identify mutated antigens recognized by adoptively transferred tumor-reactive T cells", Nature Medicine, 2013, vol. 19, pp. 747-752.
Rooney et al., "Molecular and Genetic Properties of Tumors Associated with Local Immune Cytolytic Activity", Cell, 2015, vol. 160, No. 1-2, pp. 48-61.
Strønen et al., "Targeting of cancer neoantigens with donor-derived T cell receptor repertoires", Cancer Immunotherapy, 2016, vol. 352, No. 6291, pp. 1337-1341.
International Preliminary Report on Patentability received for PCT Application Serial No. PCT/US2017 /064078, dated Jun. 13, 2019, 6 pages.
Declaration of Non-Establishment of International Search Report and Written Opinion received for PCT Application Serial No. PCT/US2017 /064078, dated Feb. 22, 2018, 4 pages.
Snyder et al., "Genetic Basis for Clinical Response to CTLA-4 Blockade in Melanoma", New England Journal of Medicine, 2014, vol. 371, No. 23, pp. 2189-2199.
International Search Report and Written Opinion received for Singaporean Patent Application Serial No. 11201904934X dated Sep. 4, 2020, 9 pages.
Office Action received for Korean Application Serial No. KR1020197018904, dated Jul. 7, 2020, 11 pages (Including English Translation).
Paul et al., "HLA Class I Alleles Are Associated with Peptide-Binding Repertoires of Different Size, Affinity, and Immunogenicity", The Journal of Immunology, Nov. 4, 2013, 10 Pages.
Buhler et al., "HLA DNA Sequence Variation among Human Populations: Molecular Signatures of Demographic and Selective Events", Plos One, vol. 6, Issue 2, Feb. 2011, pp. 1-16.
Fritsch et al., Cancer Immunol Res. Jun. 2014; 2(6): 522-529.
Pavlos et al., "Shared peptide binding of HLA Class I and II alleles associate with cutaneous nevirapine hypersensitivity and identify novel risk alleles", Scientific Reports, Aug. 17, 2017, pp. 1-12.
Shulka, Sachet Ashok, "Topics in cancer genomics", Iowa State University Digital Repository, 2014, 110 pages.

SEQUENCE LISTING

```
<160> NUMBER OF SEQ ID NOS: 12

<210> SEQ ID NO 1
<211> LENGTH: 9
<212> TYPE: PRT
<213> ORGANISM: Artificial Sequence
<220> FEATURE:
<223> OTHER INFORMATION: tumor antigen 1

<400> SEQUENCE: 1

Val Val Gly Ala Val Gly Val Gly Lys
1               5

<210> SEQ ID NO 2
<211> LENGTH: 9
<212> TYPE: PRT
<213> ORGANISM: Artificial Sequence
<220> FEATURE:
<223> OTHER INFORMATION: tumor antigen 2

<400> SEQUENCE: 2

Tyr Lys Leu Val Val Val Gly Ala Val
1               5

<210> SEQ ID NO 3
<211> LENGTH: 9
<212> TYPE: PRT
<213> ORGANISM: Artificial Sequence
<220> FEATURE:
<223> OTHER INFORMATION: tumor antigen 3

<400> SEQUENCE: 3
```

His Val Lys Ile Thr Asp Phe Gly Arg
1               5

<210> SEQ ID NO 4
<211> LENGTH: 9
<212> TYPE: PRT
<213> ORGANISM: Artificial Sequence
<220> FEATURE:
<223> OTHER INFORMATION: tumor antigen 4

<400> SEQUENCE: 4

Lys Ile Thr Asp Phe Gly Arg Ala Lys
1               5

<210> SEQ ID NO 5
<211> LENGTH: 9
<212> TYPE: PRT
<213> ORGANISM: Artificial Sequence
<220> FEATURE:
<223> OTHER INFORMATION: tumor antigen 5

<400> SEQUENCE: 5

Ile Thr Asp Phe Gly Arg Ala Lys Leu
1               5

<210> SEQ ID NO 6
<211> LENGTH: 9
<212> TYPE: PRT
<213> ORGANISM: Artificial Sequence
<220> FEATURE:
<223> OTHER INFORMATION: tumor antigen 6

<400> SEQUENCE: 6

Leu Val Val Val Gly Ala Asp Gly Val
1               5

<210> SEQ ID NO 7
<211> LENGTH: 9
<212> TYPE: PRT
<213> ORGANISM: Artificial Sequence
<220> FEATURE:
<223> OTHER INFORMATION: tumor antigen 7

<400> SEQUENCE: 7

Val Val Gly Ala Asp Gly Val Gly Lys
1               5

<210> SEQ ID NO 8
<211> LENGTH: 9
<212> TYPE: PRT
<213> ORGANISM: Artificial Sequence
<220> FEATURE:
<223> OTHER INFORMATION: tumor antigen 8

<400> SEQUENCE: 8

Ala Val Gly Val Gly Lys Ser Ala Leu
1               5

<210> SEQ ID NO 9
<211> LENGTH: 9
<212> TYPE: PRT
<213> ORGANISM: Artificial Sequence
<220> FEATURE:
<223> OTHER INFORMATION: tumor antigen 9

<400> SEQUENCE: 9

Leu Val Val Val Gly Ala Val Gly Val

```
<210> SEQ ID NO 10
<211> LENGTH: 9
<212> TYPE: PRT
<213> ORGANISM: Artificial Sequence
<220> FEATURE:
<223> OTHER INFORMATION: tumor antigen 10

<400> SEQUENCE: 10

Gly Ala Val Gly Val Gly Lys Ser Ala
1               5

<210> SEQ ID NO 11
<211> LENGTH: 9
<212> TYPE: PRT
<213> ORGANISM: Artificial Sequence
<220> FEATURE:
<223> OTHER INFORMATION: tumor antigen 11

<400> SEQUENCE: 11

Asn Leu Leu Gly Arg Asn Ser Phe Lys
1               5

<210> SEQ ID NO 12
<211> LENGTH: 9
<212> TYPE: PRT
<213> ORGANISM: Artificial Sequence
<220> FEATURE:
<223> OTHER INFORMATION: tumor antigen 12

<400> SEQUENCE: 12

Lys Val Arg Val Cys Ala Cys Pro Gly
1               5
```

TUMOR ANTIGENICITY PROCESSING AND PRESENTATION

This application claims priority to U.S. provisional application with the Ser. No. 62/428,945, filed Dec. 1, 2016, and which is incorporated by reference herein.

FIELD OF THE INVENTION

The field of the invention is computational analysis of omics data to predict treatment options, especially as it relates to selection of target epitopes in neoepitope-based immune therapy.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Cancer immunotherapies targeting certain antigens common to a specific cancer have led to remarkable responses in some patients. Unfortunately, many patients failed to respond to such immunotherapy despite apparent expression of the same antigen or existence of specific mutation that can give rise to antigens. One possible reason for such failure could be that antigens may vary, in other words, may contain different point mutations among different patients such that a treatment method designed to target the antigen having one type of mutation may not be effective to target the antigen having another type of mutation. Another possible reason could be that human leukocyte antigen (HLA) variability among patients may have led to insufficient processing of the antigen and/or antigen display on the cell surface such that the antigen may not be exposed to the treatment and/or immune system.

To increase the selection of specific targets for immune therapy, attempts have been made to introduce random mutations in one or more specific cancer-related genes to generate a library or group of tumor specific antigens (neoepitopes) that can trigger cytolytic T-cell responses. In addition, some efforts have been made to determine whether these neoepitopes generated by random mutations are likely to be presented with MHC proteins encoded by various alleles. For example, U.S. Patent Pub. No. 2016/0339090 to Hacohen discloses that binding affinities of 9-mer or 10-mer peptides generated by random mutations (missense mutations) to 9 different known HLA allotypes of chronic lymphomatic leukemia patients were predicted using netMHC-pan to find that a majority of those 9-mer or 10-mer peptides had affinities below 500 nM to the different known HLA allotypes.

Others also tried to identify associations of tumor type and mutated sequences with various HLA alleles that are present at different frequencies in different ethnicities. For example, International Pat. App. No. PCT/US2016/033452 to Fritsch discloses that a group of wild type and mutant 9-mer peptide antigens bind with different binding affinities to specific types of HLA allotypes, some of which are preferentially or more frequently found in specific ethnicity (e.g., Caucasian, Asian, etc.). Fritsch also identified one or more potential HLA allotypes that may present the antigens with specific mutant sequences of cancer-related genes by binding to the antigen with a predicted affinity of under 500 nM. However, these attempts are mostly limited to analysis of a single antigen derived from a single gene with respect to multiple HLA allotypes. Thus, it cannot be readily determined whether any one of antigens with different mutations derived from a single gene will qualify as a therapeutically effective target for immunotherapy for a patient. In other words, the known art cannot readily provide a prioritized target among a patient's antigens for effective immunotherapy.

Therefore, even though multiple methods of identification of neoepitopes that preferentially bind to specific HLA allotypes are known in the art, all or almost all of them suffer from one or more disadvantage. Consequently, it would be desirable to have improved systems and methods for tumor antigen identification that increases the likelihood of a therapeutic response in immune therapy.

SUMMARY OF THE INVENTION

The inventive subject matter is directed to various systems and methods to identify a tumor antigen that is predicted to be presented on a patient's tumor cell such that an immunotherapy for a cancer can be effectively designed and conducted by targeting the tumor antigen. Most typically, the target antigen is selected based on the patient's HLA allele type and a mutation of a cancer driver gene in the patient's tumor by comparing or matching those with an HLA allele that is frequently found in a population and binds to the mutation. Thus, in one particularly preferred aspect, the inventors contemplate a method of targeting a tumor antigen in a patient for immune therapy of a cancer. In this method, a patient's omics data is obtained from the patient's tumor tissue, and a presence of at least one mutation in a cancer driver gene that gives rise to the tumor antigen can be identified using the patient's omics data. The patient's HLA allele type is also determined, preferably from the patient's tumor tissue. Then, the patient's HLA allele type and the tumor antigen can be matched with a majority allele type having a minimum affinity to the same tumor antigen. Upon matching, a cancer vaccine targeting the tumor antigen can be administered to the patient.

Most typically, the majority allele type represents a majority allele type among different ethnicities, different geographic locations, different gender, or family provenance. In a preferred embodiment, the majority allele type has a population frequency of at least 0.1% in a plurality of ethnicities or at least one of the ethnicities. Alternatively, the majority allele type has a population frequency that is in a top quartile in a plurality of ethnicities or in at least one of the ethnicities. With such majority allele types, it is preferred that the minimum affinity is determined by comparing affinities to the tumor antigen with respect to a plurality of HLA alleles. Alternatively, the minimum affinity can be determined by a $K_d$ of equal of less than 100 nM.

In another aspect of the inventive subject matter, the inventors contemplate a method of targeting a tumor antigen in a patient for immune therapy of a cancer. In this method, a patient's omics data is obtained from the patient's tumor tissue, and a presence of at least one mutation in a cancer driver gene that gives rise to the tumor antigen can be identified using the patient's omics data. The patient's HLA allele type is also determined, preferably from the patient's tumor tissue. Then, the patient's HLA allele type and the tumor antigen can be matched with HLA allele types and mutation sequences of a plurality of patients who had been diagnosed with at least one type of cancer and treated with at least one cancer treatment. Upon matching, a cancer treatment can be administered to the patient based on the matching.

Various objects, features, aspects and advantages of the inventive subject matter will become more apparent from the following detailed description of preferred embodiments, along with the accompanying drawing figures in which like numerals represent like components.

DETAILED DESCRIPTION

Figure 1:
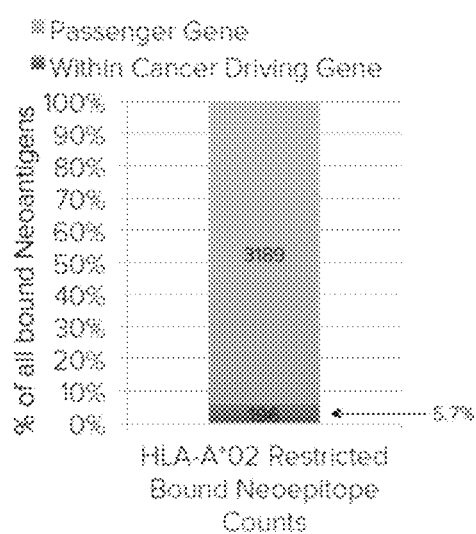
FIG. 1 is a bar graph depicting the percentage of neoepitopes within cancer driving genes and passenger genes.

HLA is a highly polymorphic gene complex that encodes the major histocompatibility complex (MHC) proteins in humans. So far, more than 4,000 HLA alleles in human gene are identified, which provides a large diversity of the HLA alleles among individuals. More recently, demographical studies have shown that frequencies of various HLA alleles can be stratified based on major ethnicities, geographical region of the population, or family heritage, indicating that susceptibilities to commonly occurring cancer types or immune-related diseases in such ethnicities, geographical region, or a family may be closely related with frequent HLA allele types present in those population groups.

Such large variety of HLA alleles results from polymorphic variations in a nucleic acid segment encoding an antigen binding domain of the MHC protein. With that, the inventors investigated whether various HLA allotypes encoded by different HLA alleles may be responsible for differentially presenting various cancer antigens on the cancer cell such that differential immune response can be triggered toward the tumor cells having the same mutation. The inventors found that HLA allotypes encoded by different HLA alleles shows different binding affinities to the same tumor antigen. The inventors further surprisingly found that HLA allotypes encoded by different HLA alleles may show preferential binding to one tumor antigen among various tumor antigens derived from a mutation of a cancer driver gene.

With that, the inventors have now discovered that cancer antigen-based immune therapy or neoepitope-based immune therapy can be further improved by targeting the tumor antigen that has a high probability to be presented on the patient's tumor cells with the patient-specific HLA allele type. The inventors further discovered the high probability can be determined or predicted by matching the patient's HLA allele information with at least one or a plurality of HLA alleles frequently found in a group of population associated with one or more type of cancers more frequently found in such group of population.

As used herein, the term "tumor" refers to, and is interchangeably used with one or more cancer cells, cancer tissues, malignant tumor cells, or malignant tumor tissue, that can be placed or found in one or more anatomical locations in a human body.

As used herein, the term "bind" refers to, and can be interchangeably used with a term "recognize" and/or "detect", an interaction between two molecules with a high affinity with a $K_D$ of equal or less than $10^{-6}$M, or equal or less than $10^{-7}$M.

As used herein, the term "provide" or "providing" refers to and includes any acts of manufacturing, generating, placing, enabling to use, or making ready to use.

Cancer Driver Genes and Mutations

As used herein, the tumor antigens include any peptide antigens or non-peptide antigen (e.g., lipid antigens, etc.) that are expressed by the tumor cells that can trigger immune response in the patient when expressed on the tumor cell surface. It is contemplated that tumor antigens can be encoded by a cancer driver gene or cancer passenger gene. As used herein, the cancer driver gene refers to a gene whose mutation(s) triggers or increases cell growth, preferably net tumor cell growth. Thus, for example, a cancer driver gene can be a tumor suppressor gene, an oncogene, receptor genes, one or more signal transduction genes, transcription regulator genes, or a cell-cycle related gene. The cancer passenger gene, in contrast, refers a gene whose mutation(s) does not directly trigger or increase cell growth, preferably net cell growth. For example, the passenger gene may include some type of genes involved in cell metabolism, trafficking, subcellular organelle structural genes, and so on.

As shown in FIG. 1, a majority of tumor antigens (e.g., neoantigens) are found to be derived from passenger genes, while significantly less than 10% of tumor antigens are found to be derived from a cancer driver gene. While the proportion of the cancer driver gene antigens is small, it is contemplated that targeting a cancer driver gene is thought to provide an enhanced therapeutic effect as an immune response against a protein encoded by a cancer driver will not only promote a cell-based cytotoxic effect against tumor cells, but also facilitate functional interference with the protein encoded by the cancer driver gene. For example, where the cancer driver gene is KIT (mast/stem cell growth factor receptor) and includes a tumor antigen, an antibody binding to the KIT tumor antigen may not only tag the protein for cytotoxic destruction by NK cells, NKT cells, or T cells, but may also inhibit signaling through the receptor pathway and as such inhibit cancer driver function. Thus, most preferred tumor antigens to target with immunotherapy would be those located in a protein or a polypeptide that is encoded by a known, predicted, or suspected cancer driver gene that has a known or predicted mutation.

It is contemplated that tumor driver genes are associated with at least one or more cancer types such that one or more mutations in one cancer drive gene can be found in one type of cancer than another. For example, mutations in BRCA1 gene is more frequently found in breast tumors in breast cancer patients than other type of cancer types. Suitable cancer types include BLCA, BRCA, CESC, COAD, DLBC, GBM, HNSC, KICH, KIRC, KIRP, LAML, LGG, LIHC, LUAD, LUSC, OV, PRAD, READ, SARC, SKCM, STAD, THCA, and UCEC.

With respect to the identification or other determination (e.g., prediction) of a gene as being a cancer driver gene, various methods and prediction algorithms are known in the art, and are deemed suitable for use herein. For example, suitable algorithms include MutsigCV (*Nature* 2014, 505 (7484):495-501), ActiveDriver (*Mol Syst Biol* 2013, 9:637), MuSiC (*Genome Res* 2012, 22(8):1589-1598), Oncodrive-Clust (*Bioinformatics* 2013, 29(18):2238-2244), OncodriveFM (*Nucleic Acids Res* 2012,40(21):e169), OncodriveFML (*Genome Biol* 2016, 17(1):128), Tumor Suppressor and Oncogenes (TUSON) (*Cell* 2013, 155(4): 948-962), 20/20+ (https://github.com/KarchinLab/2020plus), and oncodriveROLE (*Bioinformatics* (2014) 30 (17): i549-i555).

Cancer driver genes can also be identified using probabilistic pathway analysis tools, and especially preferred tools include PARADIGM (*Bioinformatics*, 2010, vol. 26 (pg. i237-i245)). PARADIGM assesses the activity of a gene in the context of a genetic pathway diagram $\phi$ by drawing inferences from a dataset of observations D. The pathway diagram $\phi$ describes connections between hidden gene expression variables, their corresponding observational data, and any regulatory inputs and outputs. Variables are connected to each other by factors, which encode probabilistic dependencies constraining mutually connected variables. PARADIGM then uses a belief-propagation algorithm on a factor graph derived from $\phi$ to compute inferred pathway levels (IPLs) for each gene, complex, protein family and cellular process by combining gene expression, copy number and genetic interactions. Positive IPLs reflect how much more likely the gene is active in a tumor (and as such may be a cancer driver gene), and negative IPLs how likely the gene is inactive in the tumor relative to normal. Such methods can be further refined by calculating a Shift (PARADIGM-SHIFT) score that is based on the intuition of comparing the observed downstream consequences of a gene's activity to what is expected from its regulatory inputs as is described elsewhere (*Bioinformatics* (2012) 28 (18): i640-i646).

Alternatively, or additionally, identification of cancer driver genes may also employ various sources for known cancer driver genes and their association with specific cancers. For example, the Intogen Catalog of driver mutations (2016.5; URL: www.intogen.org) contains the results of the driver analysis performed by the Cancer Genome Interpreter across 6,792 exomes of a pan-cancer cohort of 28 tumor types. Validated oncogenic mutations are identified according to the state-of-the-art clinical and experimental data, whereas the effect of the mutations of unknown significance is predicted by the OncodriveMUT method. Similarly, the Intogen Cancer Drivers Database (2014.12; URL: www.intogen.org) contains information on the genes identified as drivers in Rubio-Perez and Tamborero et al. (*Cancer Cell* 27 (2015), pp. 382-396).

The exemplary list of cancer driver gene is shown in Table 1.

TABLE 1

| Gene symbol | Tumor type |
|---|---|
| AURKA | COREAD |
| BAP1 | BRCA |
| BAP1 | BRCA |
| BAP1 | LGG |
| BRCA1 | BRCA |
| BRCA2 | BRCA |
| CCND2 | COREAD |
| CCND2 | GBM |
| CCND3 | COREAD |
| CCNE1 | BLCA |
| CCNE1 | BRCA |
| CCNE1 | OV |
| CCNE1 | UCEC |
| CDK4 | GBM |
| CDK4 | LGG |
| CDK4 | LUAD |
| CDK4 | CM |
| CDK4 | CM |
| CDK6 | GBM |
| CDK6 | LUSC |
| CDKN1B | BRCA |
| CDKN1B | BRCA |
| CDKN1B | PRAD |
| CDKN1B | PRAD |
| CDKN2A | BLCA |
| CDKN2A | BLCA |
| CDKN2A | BRCA |
| CDKN2A | GBM |
| CDKN2A | HNSC |
| CDKN2A | HNSC |
| CDKN2A | RCCC |
| CDKN2A | LGG |
| CDKN2A | LUAD |
| CDKN2A | LUAD |
| CDKN2A | LUSC |
| CDKN2A | LUSC |
| CDKN2A | CM |
| CDKN2A | CM |
| CDKN2B | BLCA |
| CDKN2B | BRCA |
| CDKN2B | GBM |
| CDKN2B | RCCC |
| EGFR | BLCA |
| EGFR | BRCA |

TABLE 1-continued

| Gene symbol | Tumor type |
| --- | --- |
| EGFR | GBM |
| EGFR | HNSC |
| EGFR | HNSC |
| EGFR | LGG |
| EGFR | LGG |
| EGFR | LUAD |
| EGFR | LUAD |
| EGFR | LUSC |
| EGFR | LUSC |
| ERBB2 | BLCA |
| ERBB2 | BRCA |
| ERBB2 | BRCA |
| ERBB2 | COREAD |
| ERBB2 | UCEC |
| FBXW7 | BLCA |
| FBXW7 | HNSC |
| FBXW7 | LUSC |
| FGFR1 | HNSC |
| FGFR2 | STAD |
| FGFR3 | BLCA |
| FGFR3 | BLCA |
| FGFR3 | GBM |
| FGFR3 | UCEC |
| IGF1R | BRCA |
| IGF1R | OV |
| MDM2 | BLCA |
| MDM2 | GBM |
| MDM2 | HNSC |
| MDM2 | LUAD |
| MDM2 | CM |
| MDM4 | GBM |
| MDM4 | LGG |
| MET | GBM |
| MET | GBM |
| MET | RCCC |
| MET | LUAD |
| MET | STAD |
| NF1 | BRCA |
| NF1 | AML |
| NF1 | AML |
| NF1 | OV |
| NF1 | OV |
| NF1 | UCEC |
| NF2 | CM |
| NF2 | UCEC |
| PTEN | BRCA |
| PTEN | BRCA |
| PTEN | COREAD |
| PTEN | COREAD |
| PTEN | GBM |
| PTEN | GBM |
| PTEN | HNSC |
| PTEN | RCCC |
| PTEN | LUSC |
| PTEN | LUSC |
| PTEN | OV |
| PTEN | PRAD |
| PTEN | PRAD |
| PTEN | CM |
| PTEN | CM |
| PTEN | STAD |
| PTEN | THCA |
| PTEN | UCEC |
| PTEN | UCEC |
| SMARCA4 | BRCA |
| SMARCB1 | PRAD |
| STK11 | BRCA |
| STK11 | HNSC |
| STK11 | LUSC |
| STK11 | LUSC |
| STK11 | OV |
| TP53 | BRCA |
| TP53 | AML |
| TP53 | PRAD |
| TP53 | PRAD |
| TP53 | THCA |

Further exemplary cancer driver genes for particular cancers and suitable for use in conjunction with the teachings presented herein include the following:

ALL (acute lymphocytic leukemia) driver genes include CNOT1, CNOT3, FBXW7, FLT3, KRAS, NF1, NRAS, PTEN, RB1, RPL5, SH2B3, and TP53.

AML (acute myeloid leukemia) driver genes include ASXL1, BCOR, CBFB, CEBPA, CHD4, CUL1, DIS3, DNMT3A, EGFR, EZH2, FLT3, IDH1, IDH2, KDM6A, KIT, KRAS, MED12, NF1, NPM1, NRAS, PHF6, PRPF8, PTPN11, RAD21, RUNX1, STAG2, SUZ12, TET2, THRAP3, TP53, U2AF1, and WT1.

BLCA (bladder cancer) driver genes include ACSL6, ACTB, ACTG1, ADAM10, AFF4, AHNAK, AHR, ANK3, APC, AQR, ARFGAP1, ARFGEF2, ARHGAP26, ARHGAP35, ARID1A, ARID1B, ATR, BAP1, BCLAF1, BCOR, BLM, BMPR2, BRAF, BRCA1, CAD, CARM1, CASP8, CAST, CAT, CCAR1, CCT5, CDH1, CDK12, CDKN1A, CDKN1B, CDKN2A, CEP290, CHD3, CHD9, CHEK2, CIC, CLASP2, CLSPN, CLTC, CNOT1, COPS2, CSDE1, CTCF, CTNNB1, CUL2, DDX3X, DDX5, DICER1, DIS3, DLG1, EEF1B2, EIF2AK3, EIF4A2, EIF4G1, ELF1, ELF3, EP300, ERBB2IP, ERBB3, ERCC2, FAM123B, FAT1, FBXW7, FGFR2, FGFR3, FKBP5, FLT3, FN1, FUS, G3BP2, GNAS, GOLGA5, GPS2, HLA-A, HNRPDL, HRAS, HSP90AA1, HSP90AB1, HSPA8, IDH1, IREB2, IRS2, KDM6A, KEAP1, KLF6, LIMA1, MAP3K1, MAP3K4, MAP4K3, MECOM, MED12, MED24, MET, MGA, MLH1, MLL2, MLL3, MTOR, MYH10, MYH11, NAP1L1, NCF2, NCOR2, NDRG1, NFE2L2, NOTCH1, NRAS, NUP107, NUP98, PCDH18, PCSK6, PHF6, PIK3CB, PIP5K1A, PTEN, PTPRU, RAD21, RASA1, RB1, RBM5, RHOA, RPSAP58, SETD2, SETDB1, SF3A3, SF3B1, SFPQ, SMAD4, SMC1A, SOS1, SOS2, STAG1, STAG2, STK4, SUZ12, TAF1, TAOK1, TAOK2, TBL1XR1, TBX3, TGFBR2, THRAP3, TNPO1, TP53, TP53BP1, TRIO, TSC1, TXNIP, ZFP36L2, ZMYM2, and ZNF814.

BRCA (breast cancer) driver genes include ACO1, ACSL6, ACTB, ACVR1B, AFF4, AHNAK, AKAP9, AKT1, ANK3, APC, AQR, ARFGEF2, ARHGAP35, ARID1A, ARID2, ARID4B, ARNTL, ASH1L, ASPM, ATF1, ATIC, ATM, ATR, BAP1, BCOR, BMPR2, BNC2, BPTF, BRAF, BRCA1, BRCA2, CAD, CARM1, CASP8, CAST, CBFB, CCAR1, CCT5, CDH1, CDK12, CDKN1B, CEP290, CHD4, CHD9, CHEK2, CIC, CLASP2, CLSPN, CLTC, CNOT3, CSDE1, CSNK1G3, CTCF, CUL1, DDX3X, DDX5, DHX15, DIS3, EGFR, EIF1AX, EIF2C3, EIF4A2, EIF4G1, ELF1, EP300, ERBB2, ERBB2IP, ERCC2, FBXW7, FLT3, FMR1, FN1, FOXA1, FOXP1, FUBP1, FUS, G3BP2, GATA3, GOLGA5, GPS2, HCFC1, HLA-A, HLF, HNRPDL, HSPA8, IDH1, ITSN1, KALRN, KDM5C, KEAP1, KLF4, KRAS, LCP1, LPHN2, LRP6, MACF1, MAP2K4, MAP3K1, MAX, MECOM, MED12, MED23, MED24, MGA, MKL1, MLH1, MLL, MLL2, MLL3, MLLT4, MSR1, MTOR, MUC20, MYB, MYH11, MYH14, MYH9, NCOR1, NDRG1, NF1, NF2, NOTCH1, NOTCH2, NR4A2, NRAS, NSD1, NUP107, NUP98, PAX5, PBRM1, PCDH18, PCSK6, PHF6, PIK3CA, PIK3CB, PIK3R1, PIK3R3, PIP5K1A, POLR2B, PRKAR1A, PRKCZ, PTEN, PTGS1, PTPRU, RB1, RBBP7, RBM5, RFC4, RHEB, RPGR, RPL5, RUNX1, SEC24D, SETD2, SETDB1, SF3B1, SFPQ, SMAD4, SMARCA4, SOS1, SOS2, SPTAN1, SRGAP1, STAG1, STAG2, STIP1, STK11, STK4, SUZ12, SVEP1, TAF1, TBL1XR1, TBX3, TCF12, TCF7L2, TFDP1, TGFBR2, THRAP3, TNPO1, TOM1, TP53, TRIO, ZFP36L1, and ZFP36L2.

CLL (chronic lymphocytic leukemia) driver genes include ACTG1, ANK3, ARID1A, ATM, BCOR, CLSPN, CNOT3, CREBBP, DDX3X, EGFR, EP300, ERBB2IP, FBXW7, FGFR2, FGFR3, HNRPDL, IDH1, IRF2, KDM6A, KRAS, MED12, MLL, MLL2, MLL3, MTOR, MYD88, NCOR1, NF1, NOTCH1, NRAS, PBRM1, PLCB1, RB1, SETDB1, SF3B1, STAG2, TP53, and XPO1.

CM (cutaneous melanoma) driver genes include ACO1, ACSL3, ACTG1, ACTG2, ACVR1B, ACVR2A, AFF4, AHCTF1, AHNAK, AHR, AKT1, ANK3, AQR, ARFGAP1, ARFGEF2, ARHGAP26, ARHGAP29, ARHGAP35, ARHGEF2, ARHGEF6, ARID1B, ARID2, ASPM, ATF1, ATIC, ATP6AP2, ATRX, B2M, BAP1, BAZ2B, BCLAF1, BLM, BMPR2, BNC2, BPTF, BRAF, BRCA1, BRWD1, C15orf55, CASP1, CASP8, CAST, CAT, CBFB, CCAR1, CCT5, CDC73, CDH1, CDK4, CDKN1A, CDKN2A, CEP290, CHD1L, CHD3, CHD6, CHD9, CHEK2, CIC, CLASP2, CLCC1, CLOCK, CLSPN, CLTC, CNOT3, COL1A1, COPS2, CRTC3, CSDA, CSNK1G3, CTCF, CTNNB1, CUL1, CUL2, CUL3, CYLD, CYTH4, DDX3X, DDX5, DHX15, DICER1, DIS3, DLG1, DNMT3A, EIF1AX, EIF2AK3, EIF4A2, EIF4G1, EIF4G3, ELF1, ELF3, EP300, ERBB2IP, ERBB3, EZH2, FAF1, FANCI, FAS, FBXW7, FCRL4, FGFR3, FMR1, FN1, FOXP1, FUBP1, FXR1, G3BP2, GATA3, GNG2, GOLGA5, HDAC3, HDAC9, HLA-A, HLA-B, HLF, HNRPDL, HRAS, HSPA8, IDH1, IDH2, IREB2, IRF7, ITGA9, ITSN1, JMY, KDM5C, KDM6A, KLF4, KLF6, KRAS, LCP1, LDHA, LNPEP, LRP6, LRPPRC, MAGI2, MAP2K1, MAP2K4, MAP3K1, MAP3K11, MAP3K4, MAP4K3, MAT2A, MCM3, MCM8, MECOM, MED17, MED24, MEN1, MFNG, MKL1, MLH1, MLL3, MSR1, NCF2, NCKAP1, NCOR1, NDRG1, NF1, NF2, NFATC4, NFE2L2, NOTCH1, NPM1, NR2F2, NR4A2, NRAS, NTN4, NUP107, NUP98, PAX5, PCDH18, PERI, PHF6, PIK3C2B, PIK3CA, PIK3CB, PIK3R1, PIK3R3, PIP5K1A, PLCB1, POLR2B, POM121, PPP2R1A, PPP2R5A, PPP2R5C, PPP6C, PRRX1, PSMA6, PTEN, PTGS1, RAC1, RAD21, RAD23B, RASA1, RASA2, RB1, RBBP7, RGS3, RHEB, RHOA, RHOT1, RPL22, RPL5, RTN4, RUNX1, SEC24D, SETDB1, SF3A3, SF3B1, SFPQ, SMAD2, SMAD4, SMC1A, SMURF2, SOS1, SOS2, SOX9, SPOP, STAG1, STAG2, STK11, SUZ12, SVEP1, SYK, SYNCRIP, TAOK1, TBX3, TCF12, TCF4, TFDP1, TFDP2, TGFBR2, TJP2, TNPO1, TP53, TRERF1, USP6, VHL, VIM, WASF3, WIPF1, WNK1, WT1, XRN1, YBX1, ZC3H11A, ZFP36L2, ZMYM2, ZNF638, and ZNF814.

COREAD (colorectal adenocarcinoma) driver genes include ACO1, ACSL6, ACVR1B, AKAP9, APC, ARID1A, ARNTL, ASPM, ATM, ATRX, AXIN2, BCOR, BMPR2, BPTF, BRAF, BRWD1, CAD, CASP8, CDC73, CDK12, CDKN1B, CEP290, CHD4, CHD9, CLSPN, CNOT1, CREBBP, CTCF, CTNNB1, CUL1, DIS3, DNMT3A, EGFR, ELF3, FAM123B, FBXW7, FN1, FOXP1, FXR1, GATA3, GNAS, GOLGA5, IDH2, ITSN1, KRAS, LPHN2, MAP2K1, MAP3K4, MECOM, MED12, MED24, MGA, MLL2, MSR1, MYH10, NF1, NR2F2, NR4A2, NRAS, NTN4, NUP107, NUP98, PCBP1, PIK3CA, PIK3R1, POLR2B, PPP2R1A, PTEN, PTGS1, PTPRU, RAD21, RBM10, RTN4, RUNX1, SF3B1, SMAD2, SMAD4, SMC1A, SOS2, SOX9, SRGAP3, STAG2, SYNCRIP, TAF1, TBX3, TCF12, TCF7L2, TGFBR2, TP53, TP53BP1, TRIO, WIPF1, WT1, and ZC3H11A.

DLBC (diffuse large B cell lymphoma) driver genes include ACTB, AKAP9, ARID1A, CHD4, CREBBP, FBXO11, MLL2, MYC, SMARCA4, and TP53.

ESCA (esophageal cancer) driver genes include ACO1, ACSL6, ACVR1B, ADAM10, AFF4, AHR, ARFGEF2, ARHGAP26, ARHGAP35, ARID1A, ARID2, ARNTL, ASPM, ATM, ATR, ATRX, BAP1, BCLAF1, BLM, BPTF, CAPN7, CDH1, CDKN1B, CDKN2A, CEP290, CHD4, CIC, CLTC, CNOT1, CNOT3, CREBBP, CSNK1G3, CTNNB1, CUL3, DDX5, DLG1, EEF1A1, EGFR, EIF2AK3, EIF4G1, ELF3, EP300, ERBB2IP, ERCC2, EZH2, FBXW7, FGFR2, FLT3, HGF, HLA-B, IREB2, IRS2, ITSN1, KALRN, KDM6A, LRP6, MACF1, MAP2K4, MAP3K4, MED12, MET, MGA, MLL2, MSR1, MTOR, NCKAP1, NFE2L2, NSD1, NUP107, NUP98, PAX5, PIK3CA, PTPRU, RAD21, RBM10, RHOA, RTN4, SETD2, SF3B1, SHMT1, SMAD4, SMARCA4, SMC1A, SOX9, SPTAN1, SRGAP3, SYNCRIP, TAF1, TAOK1, TAOK2, TBX3, TP53, TP53BP1, TRIO, WT1, ZC3H11A, ZFP36L2, and ZNF814.

GBM (glioblastoma multiforme) driver genes include ACAD8, ADAM10, AKAP9, ANK3, AQR, ARFGEF2, ARHGAP35, ARHGEF6, ARID1A, ARID2, ATRX, BAP1, BPTF, BRAF, BRCA1, CAD, CARM1, CASP1, CHD8, CLOCK, CLTC, CNOT1, CSDE1, CUL1, DIS3, EGFR, EZH2, FAT1, FN1, HDAC9, HSP90AB1, IDH1, KALRN, KDM5C, KDM6A, KDR, KRAS, LRP6, MAP3K4, MAP4K3, MAX, MEN1, MET, MLL, NCF2, NCOR1, NEDD4L, NF1, NFATC4, NR2F2, NUP107, PAX5, PBRM1, PCDH18, PIK3CA, PIK3CB, PIK3R1, PRPF8, PTEN, PTPN11, RB1, RPL5, RPSAP58, SF3B1, SIN3A, SOS1, SOX9, SPTAN1, STAG2, TGFBR2, TJP1, TP53, TRIO, WT1, and ZNF814.

HC (hepatocarinoma) driver genes include ACVR2A, APC, ARHGAP35, ARID1A, ARID1B, ARID2, ASH1L, ATRX, BLM, BPTF, CEP290, CNOT1, CTNNB1, FLT3, IDH1, ITSN1, MACF1, MLL3, MYH10, NF1, NFATC4, NFE2L2, PBRM1, PIK3CA, PTEN, RTN4, SETDB1, SF3B1, TBL1XR1, and TP53.

HNSC (head and neck squamous cell carcinoma) driver genes include ACAD8, ACTB, ACTG1, ACVR2A, ADAM10, AHR, AKT1, APAF1, APC, ARFGAP1, ARFGEF2, ARHGAP35, ARHGEF6, ARID1B, ARID2, ATIC, ATM, ATP6AP2, ATR, ATRX, B2M, BAP1, BAZ2B, BCL11A, BMPR2, BNC2, BPTF, BRAF, BRCA1, BRWD1, CAD, CARM1, CASP1, CASP8, CAT, CCAR1, CCT5, CDH1, CDK12, CDKN1B, CDKN2A, CEP290, CHD9, CIITA, CLASP2, CLSPN, CNOT4, COL1A1, CSNK2A1, CTCF, CTNNB1, CUL1, CUL3, CYLD, DDX3X, DICER1, DNMT3A, EEF1A1, EGFR, EIF2C3, ELF1, ELF4, EP300, EPHA2, EZH2, FAT1, FAT2, FBXW7, FGFR2, FLT3, FMR1, FN1, FOXP1, FUBP1, G3BP2, GNAS, GPSM2, HLA-A, HLA-B, HNRPDL, HRAS, HSPA8, IREB2, IRF6, IRS2, KALRN, KDM5C, KDM6A, KLF6, LAMA2, LPHN2, MACF1, MAP3K1, MAP4K3, MED17, MEF2C, MEN1, MGA, MGMT, MLL, MLL2, MSR1, MTOR, MUC20, MYH9, NCF2, NCKAP1, NCOR1, NEDD4L, NF1, NFATC4, NFE2L2, NOTCH1, NOTCH2, NR4A2, NSD1, NUP107, PABPC3, PAX5, PBRM1, PCDH18, PIK3CA, PIK3R1, PIK3R3, POLR2B, PPP2R1A, PPP2R5C, PRPF8, PRRX1, PSIP1, RAC1, RAD21, RASA1, RASGRP1, RHOA, RPL22, RPSAP58, RUNX1, SEC24D, SF3B1, SIN3A, SMAD2, SMARCA4, SMC1A, SOX9, SPOP, SPTAN1, STAG2, STIP1, TAOK1, TAOK2, TBL1XR1, TBX3, TCF12, TCF4, TFDP1, TFDP2, TGFBR2, THRAP3, TJP2, TP53, TRIO, TRIP10, U2AF1, WHSC1, ZC3H11A, and ZNF750.

LGG (low-grade glioma) driver genes include ACO1, ARFGEF2, ARHGAP26, ARHGEF6, ARID1A, ARID1B, ARID2, ATRX, CAD, CDK12, CHEK2, CIC, DDX3X, EEF1B2, EGFR, EIF1AX, FAM123B, FAT1, FUBP1, HGF, IDH1, IDH2, KAT6B, MAX, MECOM, MET, MLL, MLL2, MTOR, NCOR1, NEDD4L, NF1, NF2, NOTCH1, PIK3CA, PIK3R1, PTEN, PTPN11, RASA1, RB1, SETD2, SMARCA4, TAF1, TCF12, TJP1, TP53, TRIO, ZMYM2, ZNF292, and ZNF814.

LUAD (lung adenocarcinoma) driver genes include ACAD8, ACO1, ACTG1, ACTG2, ACVR1B, ACVR2A, ADAM10, AFF4, AKT1, ARFGAP1, ARHGAP26, ARID1A, ATIC, ATP6AP2, BAP1, BAZ2B, BLM, BMPR2, BRAF, BRWD1, CAPN7, CARM1, CASP8, CAT, CCAR1, CCT5, CDH1, CDK12, CDKN1B, CDKN2A, CHD1L, CHEK2, CIC, CLASP2, CLSPN, CNOT3, CNOT4, COL1A1, COPS2, CREBBP, CRNKL1, CSNK1G3, CTCF, CTNNB1, CUL2, CUL3, CYLD, DDX3X, DDX5, DHX15, DNMT3A, EEF1B2, EFTUD2, EGFR, EIF2AK3, EIF2C3, EIF4A2, EIF4G1, EP300, EPHA4, EPHB2, ERBB2IP, ERCC2, EZH2, FAT1, FBXW7, FGFR2, FMR1, FN1, FUBP1, FXR1, G3BP1, G3BP2, GNAI1, GNG2, GPSM2, HLA-A, HSP90AA1, HSP90AB1, HSPA8, IDH1, IREB2, IRS2, KDM6A, KDR, KEAP1, KLF6, KRAS, LCP1, LDHA, LPHN2, MAP2K1, MAP2K4, MAP3K1, MAP3K4, MAP4K1, MAP4K3, MAX, MED17, MED24, MEN1, MET, MGA, MKL1, MLH1, MLL, MLL3, MMP2, MSR1, MYB, MYH10, NCK1, NCKAP1, NEDD4L, NF1, NF2, NFE2L2, NPM1, NRAS, NTN4, NTRK2, NUP107, NUP98, PAX5, PBRM1, PCSK6, PHF6, PIK3R1, PIK3R3, PIP5K1A, POLR2B, PPP2R1A, PPP2R5A, PRPF8, PRRX1, PSMA6, PSMD11, PTEN, PTGS1, PTPN11, RAD23B, RASA1, RB1, RBM10, RBM5, RHEB, RTN4, SETD2, SETDB1, SF3B1, SFPQ, SHMT1, SIN3A, SMAD2, SMAD4, SMARCA4, SMC1A, SOX9, SPRR3, STAG1, STIP1, STK11, STK4, SVEP1, SYNCRIP, TAOK1, TAOK2, TBL1XR1, TCF12, TCF4, TCF7L2, TFDP1, TGFBR2, TNPO1, TOM1, TP53, TP53BP1, U2AF1, UPF3B, ZMYM2, and ZNF814.

LUSC (lung small cell carcinoma) driver genes include ABL2, ACAD8, ACO1, ACSL6, ACTG2, ACVR1B, ADAM10, AFF4, AQR, ARFGEF2, ARHGEF6, ARID1A, ARID1B, ARNTL, B2M, BLM, CASP8, CAST, CCAR1, CDC73, CDH1, CDKN1A, CDKN2A, CHD1L, CHD3, CHEK2, CIC, CLASP2, CLOCK, CNOT3, CNOT4, COPS2, CSDA, CSDE1, CTNNB1, CTTN, CUL1, DDX3X, DHX15, DHX9, DLG1, EEF1A1, EGFR, EIF2C3, EIF4A2, ELF1, ERBB2IP, EZH2, FGFR2, FGFR3, FMR1, FN1, FOXP1, FUBP1, FXR1, G3BP2, GATA3, GNAI1, GOLGA5, GPSM2, HLA-A, HLF, HRAS, HSP90AA1, HSP90AB1, HSPA8, IDH1, IREB2, IRS2, ITSN1, KDM5C, KEAP1, KRAS, MAP2K1, MAP3K1, MAP3K4, MED17, MED24, MEN1, MET, MKL1, MLH1, MLL, MLL2, MUC20, MYB, NCF2, NCK1, NDRG1, NF1, NFATC4, NFE2L2, NOTCH1, NR4A2, NTN4, NUP107, NUP98, PAX5, PCDH18, PCSK6, PHF6, PIK3CA, PIK3CB, PIK3R3, PIP5K1A, PPP2R5C, PRPF8, PTEN, PTPN11, RAD21, RASA1, RB1, RBM10, RGS3, RPL5, RTN4, SEC24D, SETD2, SETDB1, SF3A3, SF3B1, SIN3A, SMAD2, SMAD4, SPTAN1, SRGAP3, STAG1, STK11, STK4, SUZ12, SYNCRIP, TAOK2, TBL1XR1, TBX3, TFDP1, TFDP2, TGFBR2, THRAP3, TJP2, TNPO1, TOM1, TP53, UPF3B, WIPF1, WT1, ZC3H11A, and ZFP36L2.

MB (medulloblastoma) driver genes include ARID1A, ARID1B, ARID2, BCLAF1, BCOR, CCAR1, CREBBP, CTNNB1, DDX3X, FBXW7, FMR1, KDM6A, MGA, MLL2, MLL3, NF1, PIK3CA, PRKAR1A, PTCH1, SMARCA4, SMO, TAF1, TCF4, and TP53.

MM (multiple myeloma) driver genes include APC, ARHGAP35, ARID2, BRAF, CASP8, CEP290, CHD9, DDX3X, FAM46C, FXR1, KRAS, MECOM, NF1, NRAS, NSD1, PIK3CA, SF3B1, and TP53.

NB (neuroblastoma) driver genes include AHR, ALK, ANK3, ARID1A, ATM, ATRX, CEP290, COL1A1, CREBBP, EIF2C3, KLF4, LRP6, MACF1, MECOM, MET, MLL2, MYCN, NF1, NOTCH1, NRAS, PBRM1, PIK3CA, PIK3CB, PTPN11, STAG1, TAF1, and TRIO.

NSCLC (non-small cell lung cancer) driver genes include AKAP9, APC, HGF, KALRN, KEAP1, KRAS, MLL3, RB1, SEC24D, SMARCA4, and TP53.

OV (ovarian cancer) driver genes include ACO1, ACTG1, AFF4, ARID1A, ASH1L, ASPM, ATF1, ATIC, ATR, ATRX, BAP1, BAZ2B, BMPR2, BRAF, BRCA1, BRCA2, CASP1, CCAR1, CCT5, CDK12, CHD1L, CHD4, CLASP2, CLSPN, CSDE1, CTNNB1, CUL2, DDX5, DLG1, DNMT3A, EIF2AK3, EIF4A2, ERBB2IP, F8, FAM123B, FBXW7, FLT3, FMR1, GNAS, GOLGA5, GPS2, HDAC3, HGF, HSP90AA1, ITSN1, KRAS, LPHN2, MAP3K4, MAP4K3, MECOM, MED12, MKL1, MLH1, MLL2, MYH10, NCKAP1, NDRG1, NF1, NOTCH1, NR4A2, NRAS, NSD1, PIK3CA, POLR2B, PTEN, RB1, RHOA, SETD2, SETDB1, SIN3A, SOS1, STAG1, STAG2, TBX3, TCF7L2, TFDP1, TGFBR2, TJP1, TOM1, TP53, TP53BP1, TRIO, and YBX1.

PAAD (pancreas adenocarcinoma) driver genes include ACVR1B, AHNAK, ANK3, ARHGAP35, ARID1A, ARID2, ATM, CREBBP, EP300, EPC1, KRAS, MAP2K4, MLL3, PBRM1, PCDH18, PCSK6, SF3B1, SMAD4, SMARCA4, TGFBR2, and TP53.

PRAD (prostate adenocarcinoma) driver genes include ADCY1, AHNAK, AKAP9, APC, AQR, ARFGAP3, ARID1B, ATIC, ATM, ATRX, BCLAF1, BCOR, BNC2, BPTF, BRAF, CASP1, CAT, CDC27, CDH1, CDKN1B, CEP290, CHD1L, CHD3, CHD4, CHEK2, CNOT1, CNOT3, CNTNAP1, CTNNB1, CUL2, CUL3, EEF1B2, EGFR, EIF2AK3, EIF4G1, EP300, ERCC2, FAT1, FGFR2, FIP1L1, FN1, FRG1, G3BP2, GNAS, HGF, HNF1A, HRAS, HSP90AB1, HSPA8, IDH1, IRS2, KDM6A, KEAP1, MECOM, MED12, MLL2, MYH10, NAP1L1, NKX3-1, NOTCH1, NOTCH2, NUP98, PCDH18, PIK3CB, PLXNA1, PRPF8, PTEN, RPSAP58, SCAI, SETDB1, SMAD4, SMARCA1, SMARCB1, SPOP, SVEP1, TAOK2, TBL1XR1, TBX3, THRAP3, TJP1, TJP2, TP53, TP53BP1, TRIO, WHSC1L1, WNT5A, ZFHX3, and ZNF814.

RCCC (renal clear cell carcinoma) driver genes include ACO1, ACTG1, AHR, AKT1, ARHGAP26, ARID1A, ARID1B, ARID2, ASH1L, ATF1, ATM, BAP1, BCLAF1, BCOR, BMPR2, CAD, CAT, CCAR1, CDC73, CDH1, CHEK2, CLTC, CNOT3, CNOT4, COPS2, CSDA, CTCF, CUL1, DDX3X, DDX5, DHX15, DICER1, DIS3, EEF1A1, EGFR, EIF2AK3, EIF2C3, EIF4A2, EIF4G1, ELF1, ERBB2IP, EZH2, FAM123B, FLT3, FMR1, FUS, G3BP2, HDAC9, HLF, HNRPDL, HSP90AB1, IDH1, ITSN1, KDM5C, KDM6A, KEAP1, LCP1, LPHN2, LRP6, MAX, MED17, MED24, MET, MGA, MKL1, MLL3, MTOR, NCOR1, NFE2L2, NTN4, NUP98, PABPC1, PBRM1, PCDH18, PCSK6, PHF6, PIK3R1, PIP5K1A, PPP2R1A, PSMA6, PSME3, PTEN, RASA1, RPL22, RPL5, SEC24D, SETD2, SHMT1, SIN3A, SMAD2, SMC1A, SOX9, SRGAP3, TAOK2, TBL1XR1, TCF12, TJP1, TJP2, TP53BP1, TRIO, VHL, WHSC1L1, WT1, ZFP36L2, and ZNF814.

SCLC (small cell lung cancer) driver genes include AHNAK, AHR, AKAP9, ANK3, ARID1A, ARID1B, ARID2, ASH1L, ASPM, ATR, ATRX, BAZ2B, BCLAF1, BMPR2, BNC2, BRWD1, CCT5, CDK12, CHD1L, CHEK2, CLSPN, CREBBP, DICER1, EIF2AK3, EP300, FAM123B, FAT1, FN1, GNAS, HGF, HSP90AB1, ITSN1, KALRN, KDM6A, MED12, MLL, MLL2, MLL3, MNDA, MSR1, MTOR, MYB, NCKAP1, NF1, NOTCH1, NR4A2, NUP107, PIK3CA, PTEN, PTPRU, RAD21, RB1, SIN3A, SOS1, SOS2, SPTAN1, TAF1, TBX3, TJP1, TP53, and ZC3H11A.

STAD (stomach adenocarcinoma) driver genes include ACAD8, ACSL6, ACTG2, ACVR1B, ACVR2A, ADAM10, AFN4, AKAP9, ANK3, APC, AQR, ARFGEF1, ARHGAP26, ARHGAP35, ARHGEF6, ARID1A, ARID1B, ARID4A, ASH1L, ATIC, ATP6AP2, ATR, ATRX, BAP1, BCOR, BPTF, BRAF, BRCA1, CAD, CAPN7, CASP8, CAT, CCAR1, CCT5, CDC73, CDH1, CDKN2A, CEP290, CHD1L, CHD3, CHEK2, CLASP2, CLOCK, CLTC, CNOT1, CNOT4, COL1A1, COPS2, CSDA, CSDE1, CSNK1G3, CTNNB1, CUL1, CUL2, CUL3, CYLD, DDX5, DHX15, DIS3, DLG1, DNMT3A, EEF1A1, EGFR, EIF2AK3, EIF4A2, EIF4G1, ELF3, EPHA1, ERBB2IP, ERCC2, EZH2, FAM123B, FAS, FBXW7, FLT3, FOXP1, FUBP1, G3BP2, GATA3, GNA11, GNAI1, GOLGA5, HDAC3, HLA-A, HLA-B, HNRPDL, HSP90AB1, IREB2, IRF2, IRS2, KDM6A, KLF4, KLF6, KRAS, LCP1, LPHN2, MACF1, MAP2K1, MAP2K4, MAP3K1, MECOM, MED12, MED17, MET, MKL1, MLH1, MSR1, MYH11, MYH9, NAP1L1, NCK1, NCKAP1, NEDD4L, NFE2L2, NR2F2, NR4A2, NSD1, NUP107, NUP98, PCSK5, PHF6, PIK3CA, PIK3CB, PIK3R1, PIP5K1A, POLR2B, PPP2R1A, PRRX1, PTEN, PTGS1, PTPN11, PTPRF, PTPRU, RAD21, RASA1, RBBP7, RBM5, RHOA, RPL22, RTN4, RUNX1, SETD2, SF3B1, SIN3A, SMAD2, SMAD4, SMARCA4, SMC1A, SOS1, SOS2, SOX9, SPOP, SRGAP3, STARD13, STIP1, STK4, SUZ12, TAF1, TAOK2, TBL1XR1, TBX3, TCF4, TCF7L2, TFDP1, THRAP3, TJP1, TJP2, TNPO1, TNPO2, TP53, TP53BP1, WIPF1, WT1, ZC3H11A, and ZMYM2.

THCA (thyroid cancer) driver genes include AHNAK, AKAP9, ARHGAP26, ARID2, BPTF, BRAF, CDK12, CHD3, CTNNB1, DICER1, EIF1AX, GNAS, HNRPDL, HRAS, KRAS, LDHA, MLL, MLL3, NCK1, NRAS, NSD1, PIK3CA, PPM1D, PPP2R1A, PRPF8, PTEN, RPSAP58, TJP1, TP53, TRIO, WIPF1, and ZC3H11A.

UCEC (uterine corpus endometrioid cancer) driver genes include ACACA, ACTB, ACTG1, AHR, AKT1, ALK, ANK3, ARAP3, ARHGAP35, ARHGEF6, ARID1A, ARID5B, ARNTL, ATF1, ATIC, ATM, ATR, AXIN1, BAZ2B, BCLAF1, BMPR2, BRAF, BRCA1, CAPN7, CARM1, CAST, CAT, CCND1, CDKN1B, CHD3, CHD4, CHD9, CHEK2, CLOCK, CLTC, CNOT4, CSNK1G3, CTCF, CTNNB1, CTNND1, CUL1, CUX1, DEPDC1B, DHX15, DHX35, DICER1, DIS3, DNMT3A, EGFR, EIF1AX, EIF2AK3, EIF2C3, EIF4A2, EIF4G1, EP300, ERBB3, FAM123B, FAS, FBXW7, FGFR2, FLT3, FOXA2, FUBP1, FXR1, G3BP2, GNAI1, GPS2, GPSM2, HDAC3, HGF, IDH1, ING1, INPP4A, INPPL1, IREB2, KDM6A, KLF4, KRAS, MAP2K4, MAP3K1, MAX, MED17, MET, MGA, MKL1, MLH1, MLH3, MUC20, MYB, MYH10, NCF2, NCKAP1, NCOR1, NDRG1, NEDD4L, NF2, NFE2L2, NR2F2, NRAS, NUP93, PCDH18, PGR, PHF6, PIK3CA, PIK3R1, PIK3R3, PLCG1, PLXNB2, PPP2R1A, PPP2R5A, PPP2R5C, PRPF8, PRRX1, PTEN, PTPN11, RAD21, RAD23B, RBBP7, RBM5, RHEB, ROBO2, RPL22, RPL5, RTN4, RUNX1, SEC31A, SHMT1, SMAD2, SMC1A, SOX17, SPOP, SRGAP3, STIP1, SUZ12, SYNCRIP, TBL1XR1, TBX3, TFDP1, TGFBR2, TP53, TP53BP1, U2AF1, VHL, WIPF1, ZC3H11A, ZFHX3, ZFP36L2, ZMYM2, and ZNF814.

Any suitable methods and sources are contemplated to identify cancer driver antigens. In one contemplated method, the cancer driver antigens or neoepitopes can be identified in a process that preferably uses patient tumor material (e.g., fresh biopsies, frozen or otherwise preserved tissue or cell samples, circulating tumor cells, exosomes, various body fluids (and especially blood), etc.). Omics analysis can then be performed on the patient samples to obtain omics data, most typically genomics data (such as whole genome sequence data, whole exome data, etc.), transcriptomics data (and especially RNAseq data), and/or proteomics data (which may be qualitative or quantitative). Therefore, suitable methods of omics analysis include nucleic acid sequencing, and particularly NGS methods operating on DNA (e.g., Illumina sequencing, ion torrent sequencing, 454 pyrosequencing, nanopore sequencing, etc.), RNA sequencing (e.g., RNAseq, reverse transcription based sequencing, etc.), and protein sequencing or mass spectroscopy based sequencing (e.g., SRM, MRM, CRM, etc.).

In one especially preferred aspect of the inventive subject matter, DNA analysis is performed by whole genome sequencing and/or exome sequencing (typically at a coverage depth of at least 10×, more typically at least 20×) of both tumor and matched normal sample. Alternatively, DNA data may also be provided from an already established sequence record (e.g., SAM, BAM, FASTA, FASTQ, or VCF file) from a prior sequence determination. Therefore, data sets may include unprocessed or processed data sets, and exemplary data sets include those having BAMBAM format, SAMBAM format, FASTQ format, or FASTA format. However, it is especially preferred that the data sets are provided in BAMBAM format or as BAMBAM diff objects (see e.g., US2012/0059670A1 and US2012/0066001A1). Moreover, it should be noted that the data sets are reflective of a tumor and a matched normal sample of the same patient to so obtain patient and tumor specific information. Thus, genetic germ line alterations not giving rise to the tumor (e.g., silent mutation, SNP, etc.) can be excluded. Of course, it should be recognized that the tumor sample may be from an initial tumor, from the tumor upon start of treatment, from a recurrent tumor or metastatic site, etc. In most cases, the matched normal sample of the patient may be blood, or non-diseased tissue from the same tissue type as the tumor.

There are numerous methods of transcriptomic analysis known in the art, and all of the known methods are deemed suitable for use herein. For example, preferred materials include mRNA and primary transcripts (hnRNA), and RNA sequence information may be obtained from reverse transcribed polyA$^+$-RNA, which is in turn obtained from a tumor sample and a matched normal (healthy) sample of the same patient. Likewise, it should be noted that while polyA$^+$-RNA is typically preferred as a representation of the transcriptome, other forms of RNA (hn-RNA, non-polyadenylated RNA, siRNA, miRNA, etc.) are also deemed suitable for use herein. Preferred methods include quantitative RNA (hnRNA or mRNA) analysis and/or quantitative proteomics analysis, especially including RNAseq. In other aspects, RNA quantification and sequencing is performed using RNA-seq, qPCR and/or rtPCR based methods, although various alternative methods (e.g., solid phase hybridization-based methods) are also deemed suitable. Viewed from another perspective, transcriptomic analysis may be suitable (alone or in combination with genomic analysis) to identify and quantify genes having a cancer- and patient-specific mutation.

Similarly, proteomics analysis can be performed in numerous manners to ascertain actual translation of the RNA of the neoepitope, and all known manners of proteomics analysis are contemplated herein. However, particularly preferred proteomics methods include antibody-based methods and mass spectroscopic methods. Moreover, it should be noted that the proteomics analysis may not only provide qualitative or quantitative information about the protein per se, but may also include protein activity data where the protein has catalytic or other functional activity. One exemplary technique for conducting proteomic assays is described in U.S. Pat. No. 7,473,532, incorporated by reference herein. Further suitable methods of identification and even quantification of protein expression include various mass spectroscopic analyses (e.g., selective reaction monitoring (SRM), multiple reaction monitoring (MRM), and consecutive reaction monitoring (CRM)). Consequently, it should be appreciated that the above methods will provide patient and tumor specific neoepitopes, which may be further filtered by sub-cellular location of the protein containing the neoepitope (e.g., membrane location), the expression strength (e.g., overexpressed as compared to matched normal of the same patient), etc.

Likewise, the computational analysis of the sequence data may be performed in numerous manners. In most preferred methods, however, analysis is performed in silico by location-guided synchronous alignment of tumor and normal samples as, for example, disclosed in US 2012/0059670A1 and US 2012/0066001A1 using BAM files and BAM servers. Such analysis advantageously reduces false positive neoepitopes and significantly reduces demands on memory and computational resources.

It should be noted that any language directed to a computer should be read to include any suitable combination of computing devices, including servers, interfaces, systems, databases, agents, peers, engines, controllers, or other types of computing devices operating individually or collectively. One should appreciate the computing devices comprise a processor configured to execute software instructions stored on a tangible, non-transitory computer readable storage medium (e.g., hard drive, solid state drive, RAM, flash, ROM, etc.). The software instructions preferably configure the computing device to provide the roles, responsibilities, or other functionality as discussed below with respect to the disclosed apparatus. Further, the disclosed technologies can be embodied as a computer program product that includes a non-transitory computer readable medium storing the software instructions that causes a processor to execute the disclosed steps associated with implementations of computer-based algorithms, processes, methods, or other instructions. In especially preferred embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges among devices can be conducted over a packet-switched network, the Internet, LAN, WAN, VPN, or other type of packet switched network; a circuit switched network; cell switched network; or other type of network.

Additionally and optionally, matching non-tumor material (e.g., patient's non-tumor tissues such as blood, non-tumor matching tissue from a healthy individual, etc.) can be obtained to compare the omics data of tumor tissue and that of matching tissue such that the any mutations identified in the patient tumor material is specific to tumor cells.

Alternatively, patient omics data may also be provided from an already established sequence record (e.g., SAM, BAM, FASTA, FASTQ, or VCF file) from a prior sequence determination. For example, computational analysis of the DNA or RNA sequence data, or other omics data to identify cancer driver gene mutation may be performed in numerous manners. In most preferred methods, however, analysis is performed in silico by location-guided synchronous alignment of tumor and normal samples as, for example, disclosed in US 2012/0059670A1 and US 2012/0066001A1 using BAM files (computer files comprising data or sequence record in BAM format) and BAM servers (e.g., servers including a processor configured to process BAM files). Such analysis advantageously reduces false positive mutations (e.g., by random polymorphism, etc.) and significantly reduces demands on memory and computational resources. Therefore, omics data sets may include unprocessed or processed data sets, and exemplary data sets include those having BAM format, SAM format, FASTQ format, or FASTA format.

Optionally, the identification of cancer driver gene mutations from the patient sample can be limited to a predetermined number of genes that are most common or strongly associated with at least one cancer type. For example, where the patient is diagnosed with a non-small cell lung cancer, instead of obtaining omics data of entire genome or entire coding genes in a patient's tumor cell to identify any possible cancer driver gene mutations, the omics data can be obtained for less than 5 genes, less than 10 genes, less than 15 genes, less than 20 genes, less than 30 genes, less than 50 genes, that have been found most frequently mutated among the non-small cell lung cancer patients, or known to be associated (clinically or via in vitro study, etc.).

Alternatively, in some embodiments, the number of genes and the type of genes can be determined via prescreening of the patient tumor sample with a cancer panel having a plurality of most frequently mutated genes to determine which gene is or is likely to be mutated in the patient tumor sample. Any suitable commercially available or custom-made cancer panels can be used. Exemplary multi-cancer panel includes, but not limited to, Invitae Multi-Cancer Panel™, Focus::NGS® Targeted NGS Panels, NovoPM™ Cancer Panels, and so on. Such optional pre-screening process can reduce the time for and amount of omics data analysis that may include other mutations or changes in the genome, RNA sequences, or proteomes that do not substantially affect the tumor development or prognosis of the cancer.

The inventors contemplate that such obtained omics data on the cancer driver gene mutations can be filtered against a priori known molecular variation such that any false positive tumor antigens that may not be specific to tumor can be determined. For example, the cancer driver gene mutations may be compared against a database that contains known human sequences (e.g., of the patient or a collection of patients) to so avoid use of a human-identical sequence. Moreover, filtering may also include removal of cancer driver gene mutation sequences that are due to SNPs in the patient where the SNPs are present in both the tumor and the matched normal sequence(s). For example, dbSNP (The Single Nucleotide Polymorphism Database) is a free public archive for genetic variation within and across different species developed and hosted by the National Center for Biotechnology Information (NCBI) in collaboration with the National Human Genome Research Institute (NHGRI). Although the name of the database implies a collection of one class of polymorphisms only (single nucleotide polymorphisms (SNPs)), it in fact contains a relatively wide range of molecular variation: (1) SNPs, (2) short deletion and insertion polymorphisms (indels/DIPs), (3) microsatellite markers or short tandem repeats (STRs), (4) multinucleotide polymorphisms (MNPs), (5) heterozygous sequences, and (6) named variants. The dbSNP accepts apparently neutral polymorphisms, polymorphisms corresponding to known phenotypes, and regions of no variation. Using such database and other filtering options as described above, identified variable sequences of cancer driver gene may be filtered to remove those known sequences, yielding a sequence set with a plurality of neoepitope sequences having substantially reduced false positives.

Variable Tumor Antigens from a Cancer Driver Gene Mutation

It is contemplated that tumor antigens, especially tumor neoepitopes, can be characterized as expressed random mutations in tumor cells that created unique and tumor specific antigens. Therefore, viewed from a different perspective, tumor antigens (or tumor neoepitopes) may include different types mutations (e.g., deletion, insertion, transversion, transition, translocation) and may have different impact on the encoded antigens based on the mutation (e.g., nonsense, missense, frame shift, etc.). Generally preferred tumor antigens (or tumor neoepitope) presented on the tumor cell surface are relatively short polypeptides with a length of between 5-30 mers, 12-25 mers, or more typically 7-11 mers, within which change(s) in the amino acid sequences reside. For example, where the tumor antigen is to be presented by the MHC-I complex, a typical neoepitope length will be about 8-11 amino acids, while the typical length of the tumor antigen for presentation via MHC-II complex will have a length of about 13-17 amino acids.

Typically, one or more mutations in the DNA sequences encoding tumor antigens are represented by one or more changed amino acids in the protein sequence of the tumor antigen. For example, where the mutation in the cancer driver gene may result in a change of single amino acid change in at least a portion of the protein encoded by the cancer driver gene. Yet, it should be appreciated that a single amino acid change in a protein may not necessarily produce a single type of antigen possessing the changed amino acid. Most typically, it is contemplated that the changed amino acid will be at or near the central amino acid position. Yet, position of the changed amino acid in the tumor antigen (or tumor neoepitope) may be other than central. For example, a typical neoepitope may have the structure of $A_4$-N-$A_4$, or $A_3$-N-$A_5$, or $A_2$-N-$A_7$, or $A_5$-N-$A_3$, or $A_7$-N-$A_2$, where A is a proteinogenic amino acid and N is a changed amino acid (relative to wild type or relative to matched normal). Thus, it should be appreciated that a single amino acid change may be presented in numerous tumor antigen sequences that include the changed amino acid, depending on the position of the changed amino acid. In other words, depending on which segments of the mutated protein are processed to generate a tumor antigen, various tumor antigens may be generated from even a single mutation.

Figure 2:
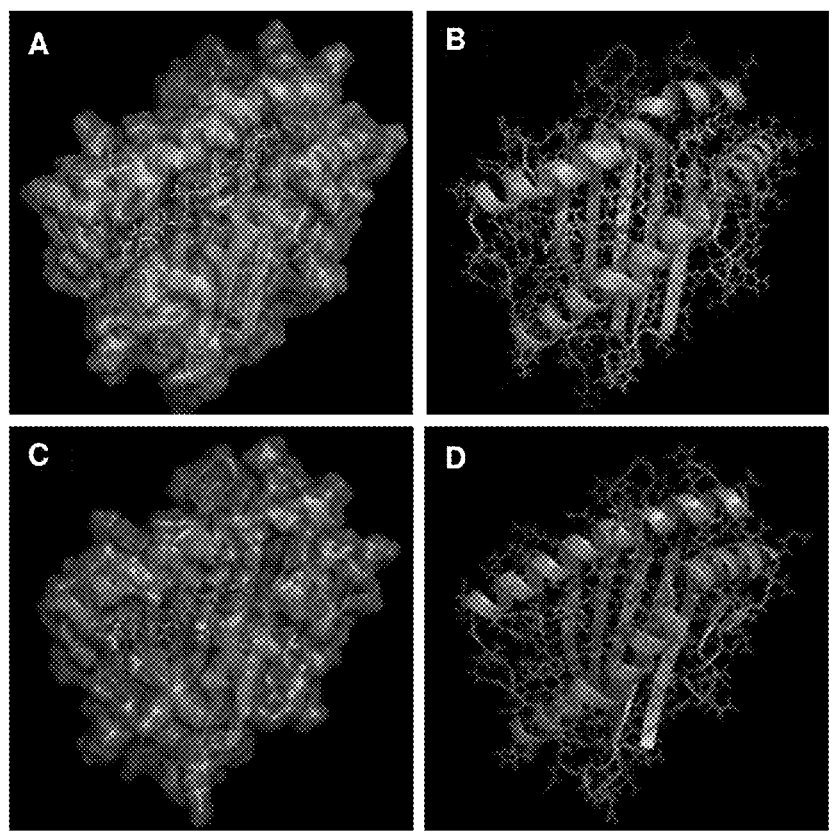
FIG. 2 shows molecular modeling of different neoantigens with the same HLA allotypes, resulting in two complexes with different stabilities.

The inventors found that various tumor antigens may have different effect in triggering immune system against the tumor antigens even if they are derived from the same single point mutation. One of the possible reasons for such different effect is that such different effects may result from different binding affinities of the antigens to MHC molecules encoded by specific HLA alleles. Another possibility is that different antigens (i.e., sharing the same mutation in different locations) may cause different conformational changes of antigen-MHC molecule complex. The inventors contemplate that some conformational changes of antigen-MHC molecule complex may cause failure of presentation of the complex on the cell surface, or reduce the interaction between the complex with the immune cells (e.g., with T cell receptor, etc.). For example, FIG. 2 shows molecular modeling of two different 9-mer neoantigens derived from KRAS G12V mutation: VVGAVGVGK and YKLVVVGAV (G12V mutation is underlined) forming a complex of MHC protein encoded by HLA-A*11:01 allele. As shown in A-B of FIG. 2, the tumor antigen VVGAVGVGK stably binds and forms a complex with the MHC protein encoded by HLA-A*11:01 allele. In contrast, as shown in C-D of FIG. 2, the complex of the tumor antigen YKLVVVGAV and the MHC protein encoded by HLA-A*11:01 allele revealed instability, indicating that different tumor antigens derived from same mutation of the same gene may have different effectiveness to trigger immune response against the tumor cells. Thus, depending on the type and stage of the cancer, it should be noted that not all of the identified tumor antigens will necessarily lead to a therapeutically equally effective reaction in a patient when the tumor antigens are targeted.

HLA Allotypes

The efficient presentation of the tumor antigen on the tumor cell surface can be achieved when the MHC molecule of the cancer cell is a match with the tumor antigen. Viewed from another perspective, a tumor antigen that can be effectively presented on the patient A's tumor cell may fail to be presented on patient B's tumor cell if the patient A and B have different HLA alleles encoding MHC molecules. Thus, the inventors contemplate that the patient's HLA allele type can be determined as a variable factor for immune therapy. Any suitable methods of determining various MHC types or HLA allele types are contemplated, including, but not limited to any chemical methods (e.g., peptide sequencing, binding assay, etc.) or any in silico methods. In a preferred embodiment, the patient's HLA allele type can be determined based on the omics data (whole genomics data, whole exome data, RNA sequence data, proteomics data). For example, in one preferred method according to the inventive subject matter, a relatively large number of patient sequence reads mapping to chromosome 6p21.3 (or any other location near/at which HLA alleles are found) is provided by a database or sequencing machine. Most typically the sequence reads will have a length of about 100-300 bases and comprise metadata, including read quality, alignment information, orientation, location, etc. For example, suitable formats include SAM, BAM, FASTA, GAR, etc. While not limiting to the inventive subject matter, it is generally preferred that the patient sequence reads provide a depth of coverage of at least 5×, more typically at least 10×, even more typically at least 20×, and most typically at least 30×.

In addition to the patient sequence reads, contemplated methods further employ one or more reference sequences that include a plurality of sequences of known and distinct HLA alleles. For example, a typical reference sequence may be a synthetic (without corresponding human or other mammalian counterpart) sequence that includes sequence segments of at least one HLA-type with multiple HLA-alleles of that HLA-type. For example, suitable reference sequences include a collection of known genomic sequences for at least 50 different alleles of HLA-A. Alternatively, or additionally, the reference sequence may also include a collection of known RNA sequences for at least 50 different alleles of HLA-A. Of course, and as further discussed in more detail below, the reference sequence is not limited to 50 alleles of HLA-A, but may have alternative composition with respect to HLA-type and number/composition of alleles. Most typically, the reference sequence will be in a computer readable format and will be provided from a database or other data storage device. For example, suitable reference sequence formats include FASTA, FASTQ, EMBL, GCG, or GenBank format, and may be directly obtained or built from data of a public data repository (e.g., IMGT, the International ImMunoGeneTics information system, or The Allele Frequency Net Database, EUROSTAM, URL: www.allelefrequencies.net). Alternatively, the reference sequence may also be built from individual known HLA-alleles based on one or more predetermined criteria such as allele frequency, ethnic allele distribution, common or rare allele types, etc.

Using the reference sequence, the patient sequence reads can now be threaded through a de Bruijn graph to identify the alleles with the best fit. In this context, it should be noted that each individual carries two alleles for each HLA-type, and that these alleles may be very similar, or in some cases even identical. Such high degree of similarity poses a significant problem for traditional alignment schemes. The inventor has now discovered that the HLA alleles, and even very closely related alleles can be resolved using an approach in which the de Bruijn graph is constructed by decomposing a sequence read into relatively small k-mers (typically having a length of between 10-20 bases), and by implementing a weighted vote process in which each patient sequence read provides a vote ("quantitative read support") for each of the alleles on the basis of k-mers of that sequence read that match the sequence of the allele. The cumulatively highest vote for an allele then indicates the most likely predicted HLA allele. In addition, it is generally preferred that each fragment that is a match to the allele is also used to calculate the overall coverage and depth of coverage for that allele.

Scoring may further be improved or refined as needed, especially where many of the top hits are similar (e.g., where a significant portion of their score comes from a highly shared set of k-mers). For example, score refinement may include a weighting scheme in which alleles that are substantially similar (e.g., >99%, or other predetermined value) to the current top hit are removed from future consideration. Counts for k-mers used by the current top hit are then re-weighted by a factor (e.g., 0.5), and the scores for each HLA allele are recalculated by summing these weighted counts. This selection process is repeated to find a new top hit. The accuracy of the method can be even further improved using RNA sequence data that allows identification of the alleles expressed by a tumor, which may sometimes be just 1 of the 2 alleles present in the DNA. In further advantageous aspects of contemplated systems and methods, DNA or RNA, or a combination of both DNA and RNA can be processed to make HLA predictions that are highly accurate and can be derived from tumor or blood DNA or RNA. Further aspects, suitable methods and considerations for high-accuracy in silico HLA typing are described in International PCT/US16/48768, incorporated by reference herein.

Most typically, the HLA-type determination using above approach includes at least three MHC-I sub-types (e.g., HLA-A, HLA-B, HLA-C) and at least three MHC-II sub-types (e.g., HLA-DP, HLA-DQ, HLA-DR, HLA-DM, HLA-DOA, HLA-DOB). In some embodiments, HLA-type of a person can be classified into each subtype by at least 2-digit depth or at least 4-digit depth. In this embodiment, HLA alleles having any sequence differences after 2-digit or 4-digit depths can be classified as the same subtypes as the binding affinities or specificities of MHC peptides encoded by such HLA alleles are expected to be substantially identical. However, in some other embodiments, greater depth (e.g., 6 digit, 8 digit) is also contemplated herein.

Identifying Matched Tumor Antigen for Designing Cancer Immune Therapy

When the patient's HLA-type and mutation(s) of one or more cancer driver gene of the patient from the patient's omics data are identified, the inventors contemplate that further computational analysis can be performed to identify the most suitable tumor antigen epitope sequence to design an effective immune therapy. In one embodiment, the inventors contemplate that all possible combinations of 9-mers or 10-mers of tumor antigen epitopes containing a point mutation (e.g., single amino acid substitution, such as EGFR L858R, etc.) can be analyzed as docking neoepitopes to the patient HLA allotypes and determining best binders (e.g., lowest $K_D$, for example, less than 500 nM, or less than 250 nM, or less than 150 nM, or less than 50 nM), for example, using NetMHC (e.g., NetMHC3.4). Of course, it should be appreciated that matching of the patient's HLA-type to the tumor antigen epitopes can be done using systems other than NetMHC, and suitable systems include NetMHC II, NetMHCpan, IEDB Analysis Resource (URL immuneepitope.org), RankPep, PREDEP, SVMHC, Epipredict, HLA-Binding, and others (see e.g., *J Immunol Methods* 2011; 374:1-4). In some embodiments, the tumor antigen epitopes (9-mer or 10-mer) can be ranked based on the binding affinities. The inventors further contemplate that the tumor antigen epitopes in a higher rank (e.g., with higher affinity to the patient's MHC type) are more likely to form a stable complex with the patient's MHC molecule, thus likely to be present on the cell surface and as such most likely to elicit an immune response with therapeutic effect.

In another and preferred embodiment, a preferred tumor antigen can be predicted by matching the HLA allele type of the patient and the tumor antigen with a majority allele type having a minimum affinity to the same tumor antigen. As used herein, a minimum affinity refers an affinity of the tumor antigen to the HLA-allele at an affinity determined by a $K_d$ of equal of less than 300 nM, preferably equal of less than 100 nM, more preferably equal of less than 50 nM.

Preferably, a majority allele type is one or more represented HLA allele type(s) among different ethnicities (Caucasians, Asians, Black, Hispanic, American Indian, etc.), different geographic locations (e.g., North America, South America, Southeast Asia, Northern Europe, Far east Asia, etc.), different genders, or family provenance (blood heritage, family relationships, etc.). In some embodiment, the majority allele type can be determined based on the frequency of the allele in the population. For example, the majority allele type in Asians may be the HLA-allele type that can be found among at least 0.05%, at least 0.1%, at least 0.3%, at least 0.5%, or at least 1% of the Asian population whose HLA-allele types are known or analyzed. In other embodiments, the majority allele type can be also determined by a quartile of the allele among all other alleles in the population. For example, where there are 1,000 HLA-allele types found among Hispanic population, the majority allele type in this population group can be defined as top 0.5%, top 1%, top 2%, or top 5% ranked based on the frequencies of the HLA allele in the population.

Grouping of populations based on the ethnicities, geographical locations or other conditions is based on the findings that such population groups show different cancer incidence rate to different type of cancers, which might indicate different susceptibilities to different type of cancers. Also, those population groups often show different types and frequencies of mutations in genes even among the same cancer type patient. Table 2 shows one exemplary statistics showing the occurrence of cancer driver gene mutations in lung adenocarcinoma patients by geographical location. In Asia, mutations in EGFR were identified in lung adenocarcinoma patients by 3.5 times higher than lung adenocarcinoma patients in USA. Instead, in USA, mutations in KRAS gene were detected 2-3 times higher than the patients in Asia. Thus, even for the same type of cancer, patients in different geographical area (or ethnicities, gender, family heritage, etc.) may show different and maybe even preferential genetic disposition leading to or contributing to the progress of the tumor, which indicates that targets for immune therapy may differ and also can be inferred based on such population groups.

TABLE 2

| Gene | USA | Asia | References |
|---|---|---|---|
| EGFR | 10% | 35% | Lynch et al. N Engl J Med. 2004 Paez et al. Science. 2004 Pao et al. PNAS 2004 |
| KRAS | 15-25% | 8% | Riley et al. Clin Cancer Res. 2008 Zheng et al. Onco Targets Ther. 2016 |

It should be also noted that HLA allele types vary in a great degree among different populations grouped by ethnicities, geographical locations, genders, or family provenance. The inventors contemplates that such variance in HLA allele types among different population groups suggests that targetable tumor antigen sequences are likely vary even among patients having the same type of cancer with same type of mutation in the same gene. As such, the inventors found that candidate tumor antigen sequences can be identified based on the HLA allele type and its frequency in the population group. Viewed from another perspective, preferred tumor antigen sequences to design an immunotherapy for a patient can be inferred or predicted from the determined HLA allele type and optionally from the patient's ethnicity, geographical locations, gender or family provenance.

In order to identify preferred tumor antigen sequences that can be an immunotherapy target for patient having different HLA allele, the inventors examined all permutations of known cancer driving mutation (single point mutation) for their affinities to frequently found HLA alleles in different ethnic groups. Tables 3-6 provide some examples of tumor antigens derived from different cancer driving mutations and its relationship with various HLA allele types identified from one or more ethnic origin. In these examples, antigens with affinities to any of the HLA allele with Kd equal or lower than 500 nM are shown. For example, Table 3 provides examples of tumor antigens derived from EGFR L585R (Leucine to Arginine point mutation at the amino acid position 585) mutation and its relationships with various HLA alleles and ethnicity. As shown, different HLA alleles are shown at a different population frequency among different origins. For example, HLA allele, A*31:01, can be found in three different ethnicities, including American Indian, Caucasoid, Mixed, and Asian. Among these four ethnicities, the highest frequency of this HLA allele shown is 0.19%. In an embodiment where the majority allele is determined as HLA alleles that are found in at least 0.1% or more of the population, and the minimum affinity is equal or less than 100 nM, the HLA allele, A*31:01, is a majority allele and has a satisfying minimum affinity to a tumor antigen sequence of HVKITDFGR at a Kd value of 12 nM. Thus, if a patient is an Asian, with a EGFR L585R mutation in the tumor cell, and has HLA allele of A*31:01, the tumor antigen sequence of HVKITDFGR can be the one that has high probability to be present on the patient's tumor cell surface with patient's MHC molecule and can be a desirable target for immune therapy.

TABLE 3

| Neo-antigens | HLA Allele | Binding Affinity (nM) | Highest Population Frequency (%) | Known Ethnic Origin Of Source |
|---|---|---|---|---|
| KITDFGRAK | A*30:01 | 48 | 0.16 | Black, Caucasoid, Asian |
| HVKITDFGR | A*31:01 | 12 | 0.19 | American Indian, Caucasoid, Mixed, Asian |
|  | A*33:01 | 48 | 0.11 | Black, Caucasoid, Asian |
|  | A*68:01 | 13 | 0.36 | Caucasoid |
| ITDFGRAKL | C*05:01 | 31 | 0.12 | Caucasoid |

For another example, Table 4 provides examples of tumor antigens derived from KRAS G12D mutation and its relationships with various HLA alleles and ethnicity. In this example, it is indicated that patients having same type of cancer and same genetic mutations, yet with different HLA alleles, may have very different outcome in immunotherapy targeting the same tumor antigen. For example, even if two patients have same type of cancer, same KRAS G12D mutation, and same Hispanic ethnicity, an immunotherapy targeting the tumor antigen sequence of LVVVGADGV may be effective to one patient with HLA-allele of A*02:06 (as having a binding affinity of 22 nM), but may not be effective to another patient with HLA-allele of A*68:02 (as having a binding affinity of 277 nM). Thus, in other words, if a patient having an HLA-allele of A*68:02, the tumor antigen with a sequence of LVVVGADGV may not predicted as an effective target for immunotherapy.

TABLE 4

| Neo-antigens | HLA Allele | Binding Affinity (nM) | Highest Population Frequency % | Known Ethnic Origin Of Source |
|---|---|---|---|---|
| LVVVGADGV | A*02:06 | 22 | 0.34 | Hispanic |
|  | A*02:50 | 23 | 0.07 | Hispanic |
|  | A*68:02 | 277 | 0.08 | Hispanic, Asian |
|  | A*69:01 | 278 | 0.01 | Black, Caucasoid, Asian |
| VVGADGVGK | A*11:01 | 194 | 0.359 | Caucasoid, Asian |

In another example, Table 5 provides examples of tumor antigens derived from KRAS G12V mutation and its relationships with various HLA alleles and ethnicity. In this example, it is indicated that one tumor antigen can be preferred over another tumor antigen (with same mutation) based on the HLA allele type of the patient for immunotherapy. For example, when a cancer patient is identified to have KRAS G12V mutation and has an HLA-allele type of A*02:50, two tumor antigens having sequences of AVGVGKSAL or LVVVGAVGV may be considered as a target for immunotherapy, and the tumor antigen having a sequence of LVVVGAVGV will be preferred and recommended as such sequence shows stronger affinity of 18 nM compared to 344 nM of the other tumor antigen (AVGVGKSAL), given the same highest population frequency.

TABLE 5

| Neo-antigens | HLA Allele | Binding Affinity (nM) | Highest Population Frequency % | Known Ethnic Origin Of Source |
|---|---|---|---|---|
| GAVGVGKSA | C*03:03 | 412 | 0.15 | American Indian, Caucasoid, Asian |
| AVGVGKSAL | A*02:50 | 344 | 0.07 | Hispanic |
|  | B*07:02 | 230 | 0.17 | Australian Aboriginal, Caucasoid, Asian |
| VVGAVGVGK | A*03:01 | 234 | 0.25 | Black, Caucasoid, Asian |
|  | A*11:01 | 50 | 0.359 | Caucasoid, Asian |
| YKLVVVGAV | A*02:11 | 77 | 0.16 | American Indian, Caucasoid, Asian |
|  | B*39:01 | 499 | 0.04 | American Indian, Asian |
|  | C*12:03 | 166 | 0.11 | Black, Caucasoid, Asian |
|  | C*14:02 | 204 | 0.09 | Caucasoid, Asian |
| LVVVGAVGV | A*02:03 | 430 | 0.17 | Asian |
|  | A*02:06 | 22 | 0.34 | Hispanic |
|  | A*02:19 | 299 | 0.01 | American Indian |
|  | A*02:50 | 18 | 0.07 | Hispanic |
|  | A*68:02 | 117 | 0.08 | Hispanic, Asian |
|  | A*69:01 | 95 | 0.01 | Black, Caucasoid, Asian |

In still another example, Table 6 provides examples of tumor antigens derived from TP53 E271K mutation and its relationships with various HLA alleles and ethnicity.

TABLE 6

| Neo-antigens | HLA Allele | Binding Affinity | Highest Population Frequency % | Known Ethnic Origin Of Source |
|---|---|---|---|---|
| NLLGRNSFK | A*03:01 | 35 | 0.25 | Black, Caucasoid, Asian |
|  | A*11:01 | 267 | 0.359 | Caucasoid, Asian |
|  | A*33:01 | 167 | 0.11 | Black, Caucasoid, Asian |
|  | A*68:01 | 233 | 0.36 | Caucasoid |
| KVRVCACPG | A*30:01 | 8 | 0.16 | Black, Caucasoid, Asian |

Viewed from different perspective, the inventors contemplate that, for several most frequently occurring mutations in several types of cancers, sets of cancer vaccines can be prepared based on high-frequency HLA-alleles and tumor antigen sequences with high affinity to those high-frequency HLA-alleles. For example, KRAS G12V mutation is one of the most frequently occurring mutations in adenocarcinoma among patients in the US. Theoretically, where the tumor antigen is 9-mer, there can be nine different sequences for the tumor antigens that include the KRAS G12V mutation. As such, 9 potentially different cancer vaccines can be made based on those different antigen sequences. However, based on Table 5, only 5 tumor antigen sequences may bind to any HLA-alleles or frequently found HLA-alleles, with a Kd at equal or lower than 500 nM. In other words, cancer vaccines against 5 tumor antigen sequences derived from KRAS G12V mutation would likely be in most need than the rest of 4 tumor possible antigens, in view of the frequency of the HLA-alleles and affinity of the antigens to those alleles.

Thus, in such embodiment, a cancer patient having a tumor with one of most frequently occurred mutations may readily identify the available cancer vaccines by matching the allele type of the patient and the tumor antigen with a majority allele type having a minimum affinity to the same tumor antigen. For example, if the patient has KRAS G12V mutation and has HLA-allele type of A*02:11, a cancer vaccine against the tumor antigen with a sequence of YKLVVVGAV can be matched to the patient's genetic profile (cancer driver mutation and HLA-allele type). Upon such matching, the patient can be administered with the cancer vaccine without a need of preparing a customized cancer vaccine that may take extra time and cost. As used herein, the term "administering" a cancer vaccine refers to both direct and indirect administration of the cancer vaccine. Direct administration of cancer vaccine is typically performed by a health care professional (e.g., physician, nurse, etc.), while indirect administration typically includes a step of providing or making the compounds and compositions available to the health care professional for direct administration.

Consequently, off-the shelf cancer immune therapeutics can be prepared in advance in which a neoantigen for a majority allotype (e.g., having a population frequency of at least 0.1, or at least 0.2, or at least 0.3, or at least 0.5) is identified that has a predetermined affinity of equal or less than 300 nM, or equal or less than 200 nM, or equal or less than 100 nM. The therapeutic (e.g., typically viral, yeast, bacterial or peptide vaccine) may then be provided to a patient having the same HLA allotype as the neoantigen. For example, using the KRAS G12D mutation data of Table 4 above, the off-the shelf cancer immune therapeutic can be administered to a patient to target the neoantigen LVVVGADGV where the patient's HLA type is A*02:06.

Alternatively and additionally, the inventors also contemplate that the patient's genetic profile (cancer driver mutation and HLA-allele type) can be matched with other patients' treatment information associated with those patients' genetic profiles. For example, a database may comprise treatment information data of a plurality of patients who has been diagnosed to have at least one or more type of cancer and treated with at least one or more type of cancer treatment. In some embodiments, the plurality of patients are stratified or grouped into several groups by ethnicity, geographical location, gender, or family provenance.

Typically, the treatment information data includes the cancer driver mutation types (e.g., KRAS G12V mutation, etc.) and the HLA-allele type of the plurality of patients. Preferably, the treatment information data further include the outcome of the cancer treatment and/or prognosis of the tumor after the cancer treatment of each patient. It is contemplated that patients sharing substantially similar genetic profiles are likely to respond similarly to cancer treatments, especially the cancer treatment targeting genetically specific markers (e.g., tumor antigens specific to a mutation, etc.). Thus, matching the genetic profiles of the patient with other patient's data allows selecting or matching any cancer treatment (e.g., cancer vaccine, etc.) that rendered most positive outcomes in other similar patients (sharing genetic profiles) to provide the patient the cancer treatment that has higher likelihood of success in treating the tumor.

The inventors further contemplate that matching the genetic profiles and treatment outcomes would provide treatment options for the patient with higher likelihood of success where the patient's tumor cells expresses more than one cancer driving gene mutations. For example, where the patient A and B's tumor cells possess a common mutation in cancer driving gene C and another common mutation in cancer driving gene D, patient A and B may not show same effectiveness in treating the tumor by targeting one of those cancer driving genes if their HLA-allele types are different. Instead, the patient A and B's mutations can be matched with mutations and treatment outcomes of other plurality of patients having the same HLA-allele types, and further be ranked as treatment candidates. For example, among the plurality of patients (e.g., at least 30%, at least 50%, at least 70%, etc.) having the same HLA-allele with patient A, a cancer treatment targeting gene A showed a better outcome (e.g., longer life expectancy, less metastasis, reduced tumor size, less symptoms, etc.), then the gene C can be ranked higher than gene D as candidates against which the cancer treatment can be designed.

Cancer Vaccines

Upon identification of cancer driver antigens that specifically bind to MHC molecules encoded by frequently found HLA-alleles, one or more immune therapeutic agents may be prepared using the sequence information of the cancer driver tumor antigens. While any suitable forms of immune therapeutic agents are contemplated, in one preferred embodiment, the identified cancer driver antigens can be formulated as a cancer vaccine. The cancer vaccine can comprise a genetically engineered bacterium (bacteria vaccine), a genetically engineered yeast (yeast vaccine), and a genetically engineered virus (virus vaccine) that are generated to include the recombinant nucleic acid encoding the cancer driver antigens. In such embodiments, recombinant nucleic acid encoding the cancer driver antigens can be placed as a cassette in a suitable expression bacterial vector, yeast vector or virus vector.

Figure 3:
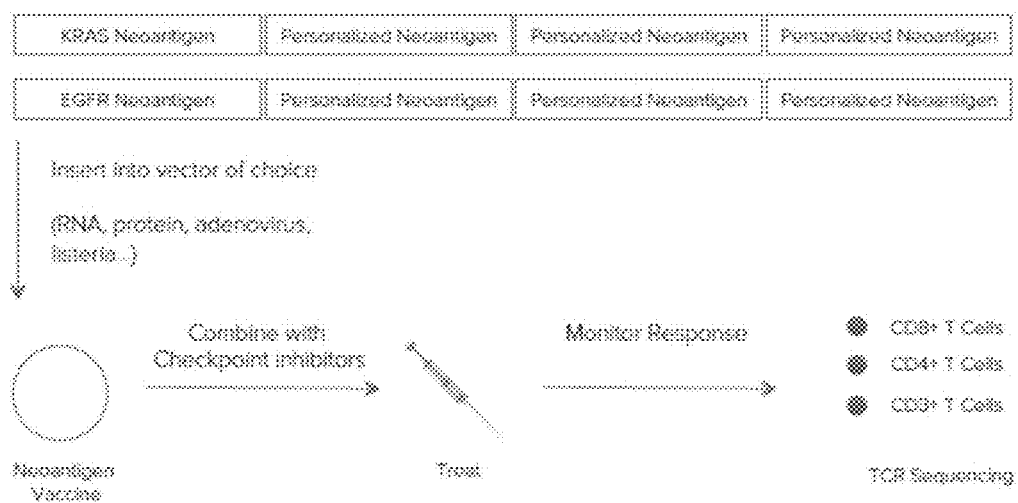
FIG. 3 is a diagram of a workflow comprising generating a polytope neoantigen vaccine using the identified neoantigens, administering the vaccine to a patient, and monitoring the immune response in the patient.

In some embodiments, the recombinant nucleic acid encoding the cancer driver antigens may include one or more nucleic acid segments encoding one or more personalized neoantigens such that the recombinant nucleic acid can encode a polytope antigen. For example, as shown in FIG. 3, the polytope antigen may include an antigen derived from the cancer driving gene mutation (e.g., KRAS, EGFR) and a plurality of personalized neoantigens. The inventors contemplate that the personalized neoantigens can be the antigen peptide or peptide fragments can be one or more inflammation-associated peptide antigens, autoimmune disease (e.g., systemic lupus erythematosus, celiac disease, diabetes mellitus type 1, Graves' disease, inflammatory bowel disease, multiple sclerosis, psoriasis, rheumatoid arthritis, etc.)-associated peptide antigen, a peptide antigen related to organ transplant rejection, a tumor associated peptide antigen, and a cancer neoepitope. Preferably, the antigen peptide or peptide fragments are patient-specific and/or tissue specific.

With respect to the bacteria vaccine, the inventors contemplate that a bacterium can be used as a fast and convenient vehicle to express human disease-related antigens in vivo to elicit immune response locally or systemically. One preferred bacterium is Escherichia coli (E. coli) for its fast growth (e.g., one complete cell cycle in 20 min) and availability of many strains optimized for protein overexpression upon inducement (e.g., lac promoter induction with IPTG, etc.). Yet, most of bacteria strains have been contemplated not suitable for introducing into the blood stream or transplanting into an organ or tissue as bacteria, in general, expresses lipopolysaccharides that triggers immune responses and causes endotoxic responses, which can lead potentially fatal sepsis (e.g., CD-14 mediated sepsis) in patients. Thus, one especially preferred bacterial strain is based on a genetically modified bacterium which expresses endotoxins at a level low enough not to cause an endotoxic response in human cells and/or insufficient to induce a CD-14 mediated sepsis when introduced to the human body.

One exemplary bacteria strain with modified lipopolysaccharides includes ClearColi® BL21(DE3) electrocompetent cells. This bacteria strain is BL21 with a genotype F-ompT hsdSB (rB-mB-) gal dcm lon λ(DE3 [lacI lacUV5-T7 gene 1 ind1 sam7 nin5]) msbA148 ΔgutQΔkdsD ΔlpxLΔlpxMΔpagPΔlpxPΔeptA. In this context, it should be appreciated that several specific deletion mutations (ΔgutQ ΔkdsD ΔlpxL ΔlpxMΔpagPΔlpxPΔeptΔ) encode the modification of LPS to Lipid $IV_A$, while one additional compensating mutation (msbA148) enables the cells to maintain viability in the presence of the LPS precursor lipid IVA. These mutations result in the deletion of the oligosaccharide chain from the LPS. More specifically, two of the six acyl chains are deleted. The six acyl chains of the LPS are the trigger which is recognized by the Toll-like receptor 4 (TLR4) in complex with myeloid differentiation factor 2 (MD-2), causing activation of NF-κB and production of proinflammatory cytokines. Lipid $IV_A$, which contains only four acyl chains, is not recognized by TLR4 and thus does not trigger the endotoxic response. While electrocompetent BL21 bacteria is provided as an example, the inventors contemplates that the genetically modified bacteria can be also chemically competent bacteria.

With respect to the yeast vaccine, the inventors contemplate that any yeast strain that can be used to produce the tumor antigen polypeptide as described above. Preferably, the yeast is a non-pathogenic strain such as Saccharomyces cerevisiae as non-pathogenic yeast strains minimize any adverse effects to the individual to whom the yeast vehicle is administered. However, pathogenic yeast may also be used if the pathogenicity of the yeast can be negated using pharmaceutical intervention. For example, suitable genera of yeast strains include Saccharomyces, Candida, Cryptococcus, Hansenula, Kluyveromyces, Pichia, Rhodotorula, Schizosaccharomyces and Yarrowia.

With respect to the virus vaccine, the inventors contemplate any suitable viral vector that can express the tumor antigen polypeptide as described above. Especially preferred expression vectors may include those that can carry a cassette size of at least 1 k, preferably 2 k, more preferably 5 k base pairs. Thus, in one embodiment, a preferred expression vector includes a viral vector (e.g., nonreplicating recombinant adenovirus genome, optionally with a deleted or non-functional E1 and/or E2b gene).

The inventors further contemplated that the recombinant virus, bacteria or yeast having recombinant nucleic acid as described above can be further formulated in any pharmaceutically acceptable carrier (e.g., preferably formulated as a sterile injectable composition) to form a pharmaceutical composition. Where the pharmaceutical composition includes the recombinant virus, it is preferred that a virus titer of the composition is between $10^4$-$10^{12}$ virus particles per dosage unit. However, alternative formulations are also deemed suitable for use herein, and all known routes and modes of administration are contemplated herein. Where the pharmaceutical composition includes the recombinant bacteria, it is preferred that the bacteria titer of the composition $10^2$-$10^3$, $10^3$-$10^4$, $10^4$-$10^5$ bacteria cells per dosage unit. Where the pharmaceutical composition includes the recombinant yeast, it is preferred that the bacteria titer of the composition $10^2$-$10^3$, $10^3$-$10^4$, $10^4$-$10^5$ yeast cells per dosage unit. In some embodiments, the virus, bacterial or yeast formulation is administered via systemic injection including subcutaneous, subdermal injection, or intravenous injection. In other embodiments, where the systemic injection may not be efficient (e.g., for brain tumors, etc.), it is contemplated that the formulation is administered via intratumoral injection.

Alternatively, immune therapy need not rely on a virus but may be effected with nucleic acid vaccination, or other recombinant vector that leads to the expression of the cancer antigens (e.g., as single peptides, tandem mini-gene, etc.) in desired cells, and especially immune competent cells.

The inventors also contemplate that a cancer vaccine may include genetically modified immune competent cells Immune competent cells include, but not limited to NK cells, modified NK cells (e.g., aNK cells, haNK cells, or taNK cells, commercially available from NantKwest, 9920 Jefferson Blvd. Culver City, Calif. 90232), NKT cells (e.g., CD1d-restricted iNKT cells, etc.), T cells, etc.) to express a chimeric antigenic receptor (CAR), specific to the tumor antigen. In some embodiments, the genetically modified immune competent cells may include a chimeric protein having an extracellular single-chain variant fragment that specifically binds the tumor antigen, an intracellular activation domain, and a transmembrane linker coupling the extracellular single-chain variant fragment to the intracellular activation domain. Preferably, the extracellular single-chain variant fragment includes variable regions of the heavy chain ($V_H$) and variable regions of the light chain ($V_L$), which are separated by a linker sequence encoding a short spacer peptide fragment (e.g., at least 10 amino acid, at least 20 amino acid, at least 30 amino acid, etc.).

Any suitable methods to identify the nucleic acid sequence of $V_H$ and $V_L$ specific to the tumor neoepitope, tumor associated antigen, or self-lipid are contemplated. For example, a nucleic acid sequence of $V_H$ and $V_L$ can be identified from a monoclonal antibody sequence database with known specificity and binding affinity to the tumor epitope. Alternatively, the nucleic acid sequence of $V_H$ and $V_L$ can be identified via an in silico analysis of candidate sequences (e.g., via IgBLAST sequence analysis tool, etc.). In some embodiments, the nucleic acid sequence of $V_H$ and $V_L$ can be identified via a mass screening of peptides having various affinities to the tumor neoepitope, tumor associated antigen, or self-lipid via any suitable in vitro assays (e.g., flow cytometry, SPR assay, a kinetic exclusion assay, etc.). While it may vary depending on the characteristics of tumor epitope, it is preferred that the optimal nucleic acid sequence of $V_H$ and $V_L$ encodes an extracellular single-chain variant fragment having an affinity to the tumor epitope at least with a $K_D$ of at least equal or less than $10^{-6}M$, preferably at least equal or less than $10^{-7}M$, more preferably at least equal or less than $10^{-8}M$. Alternatively, synthetic binders to the tumor epitope may also be obtained by phage panning or RNA display.

In other embodiments, the genetically modified immune competent cells may include a genetically modified T cell receptor complex having an α chain T cell receptor, a β chain T cell receptor, at least a portion of CD3δ, and at least a portion of CD3γ. Preferably, at least a portion of the α chain T cell receptor or a β chain T cell receptor is specific to the tumor antigen. It is especially preferred that the affinity of extracellular domain of the genetically modified T cell receptor complex to the tumor antigen is at least with a $K_D$ of at least equal or less than $10^{-6}M$, preferably at least equal or less than $10^{-7}M$, more preferably at least equal or less than $10^{-8}M$. In these embodiments, it is preferred that the intracellular activation domain includes one or more ITAM activation motifs (immunoreceptor tyrosine-based activation motif, YxxL/I-$X_{6-8}$-YXXL/I), which triggers signaling cascades in the cells expressing these motifs. Thus, upon binding to the tumor antigen, the genetically modified T cell receptor complex triggers the activation of downstream signaling cascade for triggering cytotoxicity of the immune competent cells.

The inventors also contemplate that a cancer vaccine may include the tumor antigen, or a portion of the tumor antigen in a peptide form. Optionally, the tumor antigen peptide can be coupled with a carrier protein. As used herein, a carrier protein can be any suitable polypeptide that can stably carry the load (one or more tumor antigen peptides) and preferably provide access to the tumor microenvironment when the carrier protein is administered to a patient (e.g., albumin via gp60-mediated transcytosis). Thus, preferred carrier proteins include albumin, refolded albumin, and other proteins with affinity to antibody portions (e.g., protein A, protein G, protein Z).

In some embodiments, the tumor antigen is coupled with an anchor molecule by which the tumor antigen can be coupled with the carrier protein. For example, where the carrier protein is an albumin, the anchor molecule can be a hydrophobic peptide or glycolipids in any suitable size to fit in one of Sudlow's site I and II of the albumin or any other hydrophobic area of the albumin. For example, the anchor molecule may include a hydrophobic peptide (in a length of at least 10 amino acids, 15 amino acids, 20 amino acids, 30 amino acids, etc.). In these embodiments, various configurations of the tumor antigen and hydrophobic peptides can be contemplated. For example, one tumor antigen can be directly linked to a hydrophobic peptide, or a plurality of tumor antigens can be directly linked to a hydrophobic peptide. Alternatively, one tumor antigen can be directly linked to a plurality of hydrophobic peptides or a plurality of tumor antigens can be directly linked to a plurality of hydrophobic peptides.

Alternatively, or additionally, one or more tumor antigens can be coupled with an intermediate molecule that has an anchor portion to bind to the carrier protein. In a preferred embodiment, the inventors contemplate that the intermediate molecule provides a plurality of binding sites for tumor antigens such that multiple tumor antigens can be carried via a single binding site on the carrier protein. Suitable intermediate molecule may include any protein, glycolipid, organic molecule, or inorganic molecule that does not provide any significant toxicity to the naïve tissue. For example, the suitable intermediate molecule may include a nanoparticle (e.g., quantum dots, gold nanoparticles, magnetic nanoparticles, nanotubes, polymeric nanoparticles, dendrimers, etc.), or a bead (e.g., polystyrene bead, latex bead, dynabead, etc.). Preferably, the nanoparticle and/or beads have a dimension below 1 μm, preferably below 100 nm. The nanoparticle may be crosslinked to or partially coated with a hydrophobic tail that provide an anchor to the carrier protein (e.g., albumin) One or more tumor antigens can be also crosslinked to or partially coated on the nanoparticles (e.g., via an extra tail domain linked to the tumor antigen for crosslinking, etc.).

In addition, it should also be recognized that once the neoepitope is identified as a cancer driver neoepitope, a drug may be selected that targets the protein that is encoded by the cancer driver gene harboring the cancer driver neoepitope. For example, where the cancer driver gene encodes a receptor, receptor antagonists or inhibitors or antibodies against the receptor (or its ligand) may be administered that are specific to the receptor. Similarly, where the cancer driver gene encodes a kinase, a kinase inhibitor may be administered to the patient. Therefore, it should be appreciated that identification of a cancer driver neoepitope may provide a combined treatment option that targets the mutated protein using the immune system and the function of the mutated protein.

In some embodiments, the inventors contemplate that the cancer vaccines can be co-administered with one or more co-stimulatory molecules, an immune stimulatory cytokine, and/or a protein that interferes with or down-regulates checkpoint inhibition. Suitable co-stimulatory molecules include, but not limited to, CD80, CD86, CD30, CD40, CD30L, CD40L, ICOS-L, B7-H3, B7-H4, CD70, OX40L, 4-1BBL, while other stimulatory molecules with less defined (or understood) mechanism of action include GITR-L, TIM-3, TIM-4, CD48, CD58, TL1A, ICAM-1, LFA3, and members of the SLAM family. In addition, any suitable types of cytokines to boost the immune response are contemplated. Especially preferred cytokines and cytokine analogs include IL-2, IL-15, and IL-a5 superagonist (ALT-803), IL-21, IPS1, and LMP1.

With respect to a protein that interferes with or down-regulates checkpoint inhibition, it is contemplated any suitable peptide ligands that bind to a checkpoint receptor are contemplated. Most typically, binding will inhibit or at least reduce signaling via the receptor, and particularly contemplated receptors include CTLA-4 (especially for CD8$^+$ cells), PD-1 (especially for CD4$^+$ cells), TIM1 receptor, 2B4, and CD160. For example, suitable peptide binders can include antibody fragments and especially scFv, but also small molecule peptide ligands (e.g., isolated via RNA display or phage panning) that specifically bind to the receptors. Once more, it should be appreciated that expression of the peptide molecules will preferably be coordinated such that the neoepitopes or polytope are expressed contemporaneously with one or more of the peptide ligands. Thus, it is typically contemplated that the peptide ligands are produced from a single transcript (which may or may not include the sequence portion encoding the polytope), for example, using an internal ribosome entry site or 2A sequence, or from multiple transcripts.

Optionally and additionally, the inventors further contemplate that the patient's treatment outcome can be monitored and recorded after administering the cancer vaccine. The monitoring may include evaluating the quality and/or quantity of the various immune competent cells that may elicit immune response against the cells expressing the tumor antigens. Thus, in one embodiment, the monitoring includes isolating the various immune competent cells (e.g., CD8+ T cells, CD4+ T cells, CD3+ T cells, NK cells, NKT cells, etc.) from the patient after treating the patient with cancer vaccine, for example, as least 1 day, at least 3 days, at least 5 days, at least 7 days, at least 14 days, at least 28 days after the vaccine treatment. In this embodiment, the immune competent cells expressing the T cell receptor or NK cell receptor that specifically bind to the tumor antigen can be qualitatively (e.g., by peptide sequencing of T cell receptors or NK cell receptors, etc.) and quantitatively evaluated (e.g., counting the ratio or numbers of immune competent cells specific to the tumor antigen by binding assay, etc.).

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of generating a cancer vaccine, for use in immune therapy of a cancer, the method comprising:
   obtaining, from a patient, omics data from a tumor tissue, and identifying, using computational analysis of the omics data, a presence of at least one mutation in a cancer driver gene that gives rise to a tumor antigen, wherein the omics data is selected from genomics data, transcriptomics data, and/or proteomics data, and wherein the cancer driver gene is a gene whose mutation(s) triggers or increases net tumor cell growth;
   determining, in silico, a HLA allele type of the patient;
   matching, in silico, the HLA allele type of the patient and the tumor antigen with a majority allele type having a minimum affinity to the same tumor antigen, wherein the majority allele type is one or more represented majority allele types among different ethnicities, different geographical locations, different gender, or family provenance; and
   generating a cancer vaccine that comprises a recombinant nucleic acid encoding the tumor antigen.

2. The method of claim 1, further comprising a step of filtering the at least one mutation by at least one of an a priori known molecular variation selected from the group consisting of a single nucleotide polymorphism, a short deletion and insertion polymorphism, a microsatellite marker, a short tandem repeat, a heterozygous sequence, a multinucleotide polymorphism, and a named variant.

3. The method of claim 1, wherein the cancer driver gene is in a cancer selected from the group consisting of ALL, AML, BLCA, BRCA, CLL, CM, COREAD, ESCA, GBM, HC, HNSC, LUAD, LUSC, MB, NB, NSCLC, OV, PRAD, RCCC, SCLC, STAD, THCA, and UCEC.

4. The method of claim 1, wherein the cancer driver gene is one of genes listed in Table 1.

5. The method of claim 1, wherein the matching further comprises ranking the tumor antigen based on the HLA allele type and a treatment outcome of the at least one cancer treatment.

6. The method of claim 1, further comprising administering a cancer treatment to the patient.

7. The method of claim 6, further comprising coadministering at least one of a co-stimulatory molecule, an immune stimulatory cytokine, and a protein that interferes with or down-regulates checkpoint inhibition.

8. The method of claim 6, wherein the cancer treatment is a cancer vaccine targeting the tumor antigen.

* * * * *